(12) United States Patent
Ghosh

(10) Patent No.: US 11,728,007 B2
(45) Date of Patent: Aug. 15, 2023

(54) METHODS AND SYSTEMS FOR ANALYZING NUCLEIC ACID SEQUENCES USING MAPPABILITY ANALYSIS AND DE NOVO SEQUENCE ASSEMBLY

(71) Applicant: GRAIL, LLC, Menlo Park, CA (US)

(72) Inventor: Srinka Ghosh, Menlo Park, CA (US)

(73) Assignee: GRAIL, LLC, Menlo Park, CA (US)

( * ) Notice: Subject to any disclaimer, the term of this patent is extended or adjusted under 35 U.S.C. 154(b) by 1141 days.

(21) Appl. No.: 16/206,976

(22) Filed: Nov. 30, 2018

(65) Prior Publication Data
US 2019/0172550 A1 Jun. 6, 2019

Related U.S. Application Data

(60) Provisional application No. 62/593,009, filed on Nov. 30, 2017.

(51) Int. Cl.
*G16B 20/10* (2019.01)
*G16B 20/20* (2019.01)
*G16B 30/20* (2019.01)

(52) U.S. Cl.
CPC .............. *G16B 20/10* (2019.02); *G16B 20/20* (2019.02); *G16B 30/20* (2019.02)

(58) Field of Classification Search
CPC ......... G16B 20/10; G16B 20/20; G16B 30/20
See application file for complete search history.

(56) References Cited

U.S. PATENT DOCUMENTS

| | | |
|---|---|---|
| 4,469,863 A | 9/1984 | Ts et al. |
| 5,034,506 A | 7/1991 | Summerton et al. |
| 5,216,141 A | 6/1993 | Benner et al. |
| 5,235,033 A | 8/1993 | Summerton et al. |
| 5,386,023 A | 1/1995 | Sanghvi et al. |
| 5,602,240 A | 2/1997 | Mesmaeker et al. |
| 5,637,684 A | 6/1997 | Cook et al. |
| 5,644,048 A | 7/1997 | Yau et al. |
| 6,714,874 B1 * | 3/2004 | Myers .................. G16B 30/10 707/999.102 |

(Continued)

FOREIGN PATENT DOCUMENTS

| | | | |
|---|---|---|---|
| CA | 3080170 A1 * | 6/2019 | ........... C12Q 1/6869 |
| CN | 105303068 A * | 2/2016 | |

(Continued)

OTHER PUBLICATIONS

Koehler, Ryan, et al. "The uniqueome: a mappability resource for short-tag sequencing." Bioinformatics 27.2 (2011): 272-274. (Year: 2011).*

(Continued)

*Primary Examiner* — Jesse P Frumkin
(74) *Attorney, Agent, or Firm* — Greenberg Traurig, LLP

(57) ABSTRACT

Methods of identifying changes in genomic DNA copy number are disclosed. This disclosure provides methods for detecting chromosomal aberrations in a subject using Hidden Markov modeling. In some cases, methods provided herein use de novo sequence assembly to detect chromosomal aberrations in a subject. The methods can be used to detect copy number changes in cancerous tissue compared to normal tissue. The methods can be used to diagnose cancer and other diseases associated with chromosomal anomalies.

17 Claims, 9 Drawing Sheets

(56) References Cited

U.S. PATENT DOCUMENTS

| | | | |
|---|---|---|---|
| 2003/0224384 A1 | 12/2003 | Sayood et al. | |
| 2009/0098547 A1* | 4/2009 | Ghosh | G16B 40/30 703/2 |
| 2010/0063742 A1 | 3/2010 | Hart et al. | |
| 2011/0004413 A1 | 1/2011 | Carnevali et al. | |
| 2011/0015863 A1 | 1/2011 | Pevzner et al. | |
| 2011/0257889 A1 | 10/2011 | Klammer et al. | |
| 2014/0066317 A1* | 3/2014 | Talasaz | C12N 15/1072 506/2 |
| 2014/0249764 A1* | 9/2014 | Kumar | G16B 30/00 702/20 |
| 2016/0019338 A1* | 1/2016 | Chudova | G16B 20/10 702/20 |
| 2016/0103956 A1* | 4/2016 | Conway | G16B 20/00 702/19 |
| 2016/0239602 A1* | 8/2016 | Shendure | G16B 30/00 |
| 2016/0283654 A1* | 9/2016 | Ye | G16B 20/10 |
| 2016/0292356 A1* | 10/2016 | Kim | G16B 20/10 |
| 2016/0342733 A1* | 11/2016 | Reid | G16B 20/20 |
| 2017/0270245 A1* | 9/2017 | van Rooyen | G16B 50/40 |
| 2019/0078232 A1* | 3/2019 | Ha | C12Q 1/686 |
| 2019/0267110 A1* | 8/2019 | Johnson | G16B 30/00 |
| 2019/0287645 A1* | 9/2019 | Abdueva | G16B 30/10 |

FOREIGN PATENT DOCUMENTS

| | | | | |
|---|---|---|---|---|
| WO | WO-2010127045 A2 * | 11/2010 | | G06F 19/18 |
| WO | WO-2016055971 A2 | 4/2016 | | |
| WO | WO-2021173722 A2 * | 9/2021 | | |

OTHER PUBLICATIONS

Lee, Hayan, and Michael C. Schatz. "Genomic dark matter: the reliability of short read mapping illustrated by the genome mappability score." Bioinformatics 28.16 (2012): 2097-2105. (Year: 2012).*

Derrien, Thomas, et al. "Fast computation and applications of genome mappability." PloS one 7.1 (2012): e30377. (Year: 2012).*

Beaucage et al., "The Functionalization of Oligonucleotides Via Phosphoramidite Derivatives", Tetrahedron Report No. 329, vol. 49, No. 10, 1925-1963, 1993.

Both et al., "Focal Chromosomal Copy Number Aberrations Identify CMTM8 and GPR177 as new candidate Driver Genes in Osteosarcoma", PLOS One, 1-18, Dec. 31, 2014.

Brill et al., "Synthesis of Oligodeoxynucleoside Phosphorodithioates via Thioamidites", J. Am. Chem. Soc, 111, 2321-2322, 1989.

Carlsson et al., "Screening for genetic mutations", Nature, vol. 380, 207, Mar. 21, 1996.

Carnevali, P. et al. Computational Techniques for Human Genome Resequencing Using Mated Gapped Reads. Journal of Computational Biology, 19(3):279-292 (2012).

Chin et al., "Nonhybrid, finished microbial genome assemblies from long-rea AMRT sequencing data", Nature Methods, vol. 10, No. 6, 563-569, Jun. 2013.

Chin et al., "Phased diploid genome assembly with single-molecule real-time sequencing", Nature Methods, vol. 13, No. 12, 1050-1054, Dec. 2016.

De la Bastide et al., "Assembling Genomic DNA Sequences with PHRAP", Current Protocols in Bioinformatics, 17:11.4.1-11.4.15, 2007.

Dempcy et al., "Synthesis of a thymidyl pentamer of deoxyribonucleic guanidine and binding studies with DNA homopolynucleotides", Proc. Natl. Acad. Sci, USA, vol. 92, 6097-6101, Jun. 1995.

DiGuistini et al., "De novo genome sequence assembly of a filamentous fungus using Sanger, 454 and Illumina sequence data", Genome Biology, vol. 10, issue 9, article 94, 1-12, 2009.

Drmanac, R. et al. Human Genome Sequencing Using Unchained Base Reads on Self-Assembling DNA nanoarrays. Science Reports, 327:78-81 (Jan. 1, 2010).

Drmanac, R. et al. Supporting Online Material for: Human Genome Sequencing Using Unchained Base Reads on Self-Assembling DNA Nanoarrays. Science Express, p. 1-51 (Nov. 5, 2009).

Eckstein, "Oligonucleotides and Analogues: A Practical Approach", Oxford University Press, 85-108, 1991.

Eddy, "What is a hidden Markov model?", Nature Biotechnology, vol. 22, No. 10, 1315-1316, Oct. 2004.

Egholm et al., "Peptide Nucleic Acids (PNA) Oligonucleotide Analogues with an Achiral Peptide Backbone", J. Am. Chem. Soc., 114, 1895-1897, 1992.

Etter, P. D. et al. Local De Novo Assembly of RAD Paired-End Contigs. PLoS ONE 6(4): e18561: p. 1-10 (Apr. 13, 2011).

Freeman et al., "Copy number variation: New insights in genome diversity", Genome Research, 16, 949-961, 2006.

Hiroaki Sawai, "Synthesis and Properties of Oligoadenylic Acids Containing 2'-5' Phosphoramide Linkage", Chemistry Letters, 805-808, 1984.

Horn et al., "Oligonucleotides with Alternating Anionic and Cationic Phosphoramidate Linkages: Synthesis and Hybridization of Sterouniform Isomers", Tetrahedron Letters, vol. 37, No. 6, 743-746, 1996.

Jeffs et al., "Unusual conformation of a 3'-thioformacetal linkage in a DNA duplex", Journal of Biomolecular NMR, vol. 4, 17-34, 1994.

Jenkins et al., "The Biosynthesis of Carbocyclic Nucleosides", Chem. Soc. Rev. , 169-176, 1995.

Jiang, Peiyong et al. Lengthening and shortening of Plasma DNA in hepatocellular carcinoma patients. PNAS, 112(11): E1317:1325 (Jan. 6, 2015).

Kiedrowski et al., "Parabolic Growth of a Self-Replicating Hexadeoxynucleotide Bearing a 3'-5'-Phosphoamidate Linkage", Angew. Chem. Int. Ed. Engl., vol. 30, No. 4, 423-426, 1991.

Koren et al., "Canu: scalable and accurate long-read assembly via adaptive K-mer weighting and repeat separation", Genome Research, vol. 27, No. 5, 722-736, 2017.

Koshkin et al., "LNA (Locked Nucleic Acid): An RNA Mimic Forming Exceedingly Stable LNA:LNA Duplexes", J. Am. Chem. Soc., 120, 13252-13253, 1998.

Kumar et al., "Comparing de novo assemblers for 454 transcriptome data", Genomics, 11:571, 2010.

Langmead, Ben. De Bruin Graph Assembly, Johns Hopkins Whiting School of Engineering, pp. 1-40.

Larkin et al., "Clustal W and Clustal X version 2.0", Bioinformatics, vol. 23, No. 21, 2947-2948, 2007.

Lecompte et al., "Multiple alignment of complete sequences (MACS) in the post-genomic era", Gene, 270, 17-30, 2001.

Letsinger et al., "Cationic Oligonucleotides", J. Am. Chem. Soc., vol. 110, 4470-4471, 1988.

Letsinger et al., "Effects of pendant groups at phosphorus on binding properties of d-ApA analogues", Nucleic Acids Research, vol. 14, No. 8, 3487-3499, 1986.

Letsinger et al., "Hybridization of Alternating Cationic/Anionic Oligonucleotides to RNA Segments", Nucleosides & Nucleotides, 13:6-7, 1597-1605, 1994.

Letsinger et al., "Phosphoramidate Analogs of Oligonucleotides", J. Org. Chem., vol. 35, No. 11, 3800-3803, 1970.

Li, Wentian et al. Mappability and read lenght. Frontiers in Genetics, 5(381): 1-7 (Nov. 10, 2014).

Lischer, H.E. et al. Reference-guided de novo assembly approach improves genome reconstruction for related species. BMC Bioinformatics 18:474:1-12 (2017).

Mag et al., "Synthesis and selective cleavage of an oligodeoxynucleotide containing a bridged internucleotide 5'-phosphorothioate linkage", Nucleic Acids Research, vol. 19, No. 7, 1437-1441, 1991.

Margulies et al., "Genome Sequencing in Open Micro fabricated High Density Picoliter Reactors", Nature, 437, 376-380, Sep. 15, 2005.

Meier et al., "Peptide Nucleic Acids (PNAs)—Unusual Properties of Nonionic Oligonucleotide Analogues", Chem. Int. Ed. Engl. vol. 31, No. 8, 1008-1010, 1992.

Mullan, "Multiple sequence alignment—the gateway to further analysis", Briefing in Bioinformatics, vol. 3, No. 3, 303-305, Sep. 2002.

(56) References Cited

OTHER PUBLICATIONS

Nannya et al., "A Robust Algorithm for Copy Number Detection Using High-Density Oligonucleotide Single Nucleotide Polymorphism Genotyping Arrays", Cancer Res. 65, 6071-6079, Jul. 15, 2005.
Nicholas et al., "Strategies for Multiple Sequence Alignment", BioTechniques, vol. 32, No. 3, 572-591, 2002.
Nielsen et al., "PNA hybridizes to complementary oligonucleotides obeying the Watson-Crick hydrogen-bonding rules", Letter to Nature, vol. 365, 566-568, 1993.
No Author. Complete Genomics, Data File Formats File Format v1.3,, Software v1.8.0, pp. 1-49 (2010).
Pauwels et al., "Biological Activity of New 2-5A Analogues", Chemica Scripta, vol. 26, 141-145, 1986.
Pertea et al., "TIGR Gene Indices clustering tools (TG/CL): a software system for fast clustering of large EST datasets", Bioinformatics, vol. 19, No. 5, 651-652, 2003.
Pevzner, "Computational Molecular Biology: An Algorithmic Approach", The MIT Press, 145-149, 2000.
Mesmaeker et al., "Comparison of Rigid and Flexible Backbones in Antisense Oligonucleotides", Bioorganic & Medical Chemistry Letter, vol. 4, No. 3, 395-398, 1994.
Qui et al., "Genome-wide copy number variation pattern analysis and a classification signature for non-small cell lung cancer", Genes Chromosomes Cancer, vol. 56, 559-569, 2017.
Rabiner, "A Tutorial on Hidden Markov Models and Selected Applications in Speech Recognition", Proceedings of the IEEE, vol. 77, No. 2, 257-286, Feb. 1989.
Rawls, "Optimistic About Antisense", C&E News Washington, 35-39, Jun. 2, 1997.
Sprinzl et al., Enzymatic Incorporation of ATP and CTP Analogues into the 3' End of tRNA:, Eur. J. Biochem, 81, 579-589, 1977.
Sullivant, "Algebraic Statistics", American Mathematical Society, , ISBN 0-521-85700-7, 2005.
Sun et al., "Deciphering the Correlation between Breast Tumor Samples and Cell Lines by Integrating Copy Number Changes and Gene Expression Profiles", BioMed Research International, vol. 2015, article id 901303, 11 pages, 2015.
Warren et al., "Assembling millions of short DNA sequences using SSAKE", Genome analysis, vol. 23, No. 4, 500-501, 2007.
Xiong "Essential Bioinformatics", Cambridge University Press, New York, NY, 1-8, 2006.
Zhang et al., "Identification of recurrent focal copy number variations and their putative targeted driver genes in ovarian cancer", BMC Bioinformatics, 17:222, 1-12, 2016.
Zhao et al., "PGA4 genomics for comparative genome assembly based on genetic algorithm optimization", Genomics, 94, 284-286, 2009.
Zheng et al., "iAssembler: a package for de novo assembly of Roche-454/Sanger transcriptome sequences", BMC Bioinformatics, 12:453, 1-8, 2011.

\* cited by examiner

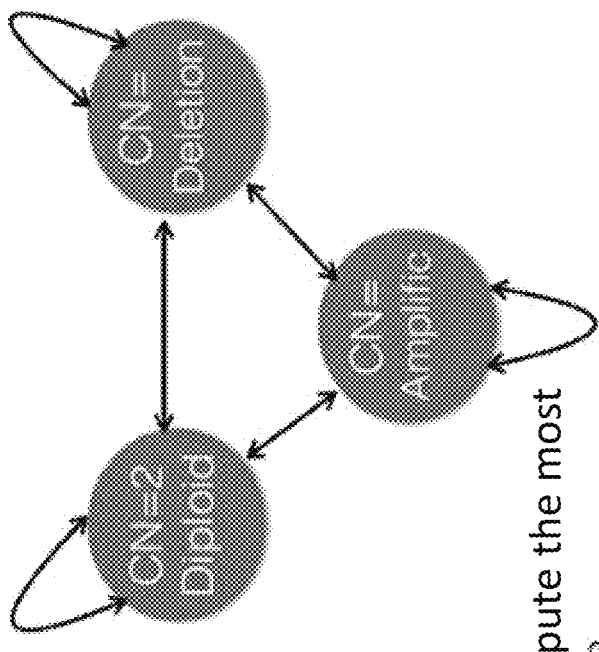

Third Step

315

- 3 state ergodic model – allowing all way transition
- Priors can be
  - ~33% each
  - or adjusted if there is family history and the cancer can have familial etiology
  - 99% for diploid
- Use expectation maximization algorithm to determine maximum likelihood estimates
- Viterbi algorithm can be used to compute the most likely path of hidden states that results in the observed state.

FIG. 3C

METHODS AND SYSTEMS FOR ANALYZING NUCLEIC ACID SEQUENCES USING MAPPABILITY ANALYSIS AND DE NOVO SEQUENCE ASSEMBLY

CROSS-REFERENCE

This application claims the benefit of U.S. Provisional Application No. 62/593,009, filed Nov. 30, 2017, which application is incorporated herein by reference in its entirety.

BACKGROUND

Chromosomal abnormalities, aberrations, and alterations can be related to many inherited diseases and traits. For example, chromosomal abnormalities can give rise to birth defects and congenital conditions and can contribute to cancer. Two types of chromosomal abnormalities include numerical or structural abnormalities. Numerical abnormalities can refer to the presence of an extra chromosome or a missing chromosome (i.e. aneuploidy). Structural abnormalities can occur when chromosomal morphology is altered. A deletion, a duplication, a translocation, such as reciprocal translocation and Robertsonian translocation, an inversion, and a ring (when a portion of a chromosome breaks off and forms a circle or ring) can be examples of structural chromosomal abnormalities. Examples of chromosomal aberrations found in cancerous cells can include gene fusions, chromosome rearrangements, and copy number variants (CNVs). Improved methods are needed for detection of chromosomal aberrations.

SUMMARY

In one aspect, the present disclosure provides a method of analyzing nucleic acid molecules from a biological sample of a subject of an organism, the method comprising: (a) obtaining, in the computer system, sequence reads of the nucleic acid molecules from the biological sample of the subject; (b) identifying, in a computer system, a first genomic region in a reference genome of the organism with a mappability score below a threshold and a second genomic region in the reference genome of the subject with a mappability score above the threshold, wherein the second genomic region is adjacent to one end of the first genomic region; (c) performing, in the computer system, local de novo assembly of a first subset of the sequence reads that align to the first genomic region and a second subset of the sequence reads that align to the second genomic region, thereby generating contigs, wherein at least one of the contigs extends over a portion of the first genomic region and a portion of the second genomic region; and (d) recovering, in the computer system, sequence data corresponding to the contigs within the first genomic region, wherein the recovered genomic sequence data comprise at least a portion of the first subset of sequence read.

In some embodiments, the method comprises identifying a third genomic region in the reference genome having a mappability score above the threshold, wherein the third genomic region is located on the other end of the first genomic region, wherein the contigs are generated by local de novo assembly of the first subset, the second subset, and the third subset of the sequence reads, and wherein at least one of the contigs extends over a portion of the first genomic region and a portion of the third genomic region.

In some embodiments, the reference genome comprises a plurality of genomic regions, and the method further comprises: (e) repeating steps (b)-(d) for each of the genomic regions having a mappability score below the threshold, thereby recovering portions of the sequence data from all of the genomic regions having mappability scores below the threshold. In some embodiments, the method further comprises combining the recovered sequence data from (e) with sequence data from genomic regions that have mappability scores above the threshold.

In some embodiments, the method further comprises normalizing the combined sequence data using a covariate of GC content. In some embodiments, the method further comprises performing statistical smoothing on the combined sequence data.

In some embodiments, the local de novo assembly is performed using an algorithm selected from the group consisting of a greedy algorithm assembler, graph method assembler, string graph assembler, De Bruijn graph assembler, Spades, Ray, ABySS, ALLPATHS-LG, and Trinity.

In some embodiments, wherein the local de novo assembly comprises creation of a scaffold comprising the contigs, and wherein the recovered sequence data align to the scaffold.

In some embodiments, wherein the sequence reads comprise paired-end sequence reads, and the scaffold is created by ordering the contigs based on paired-end information of the paired-end sequence reads.

In some embodiments, wherein the recovered sequence data comprise sequence reads that align uniquely to the contigs within the first genomic region.

In some embodiments, where the recovered sequence data further comprise sequence reads that align to genomic regions of the reference genome other than the first genomic region.

In some embodiments, the method further comprises segmenting the combined sequence data to identify a chromosomal aberration.

In some embodiments, the combined sequence data is segmented into a copy number state, the copy number state selected from the group consisting of a copy number loss state, a copy number gain state, and a copy number normal state.

In some embodiments, the copy number state comprises the copy number normal state, and wherein a variability of the copy number normal state is determined using at least one of a healthy reference sample and a tumor reference sample.

In some embodiments, the segmenting comprises using a Markov model statistical analysis. In some embodiments, the Markov model is a Hidden Markov model. In some embodiments, the Hidden Markov model comprises an ergodic model.

In some embodiments, said chromosomal aberration comprises a copy number aberration. In some embodiments, the copy number aberration is from a tumor. In some embodiments, said chromosomal aberration is identified in the absence of identifying one or more single nucleotide polymorphisms in said nucleic acid molecules.

In some embodiments, the method further comprises sequencing the nucleic acid molecules to obtain the sequence reads.

In some embodiments, the identifying the first genomic region and the second genomic region comprises comparing the mappability score of the first genomic region against the threshold and the mappability score of the second genomic region against the threshold. In some embodiments, the mappability score of the first genomic region and the second genomic region is determined according to the following:

partitioning the first genomic region into a first plurality of partitioned sequences and the second genomic region into a second plurality of partitioned sequences, and determining the mappability score of the first genomic region based, at least in part, on a first percentage of the first plurality of partitioned sequences that uniquely align to the first genomic region, and the mappability score of the second genomic region based, at least in part, on a second percentage of the second plurality of partitioned sequences that uniquely align to the second genomic region.

In some embodiments, a mappability score is one selected from the group consisting of a Broad alignability score, a Duke uniqueness score, CRG Alignability Configuration score, a Rosetta uniqueness score, and UMass uniqueness score.

In some embodiments, the nucleic acid molecules comprise cell-free nucleic acid molecules.

In another aspect, the present disclosure provides a non-transitory computer-readable medium comprising machine executable code that, upon execution by one or more computer processors, implements a method of analyzing nucleic acid molecules from a biological sample of a subject of an organism as disclosed herein.

In another aspect, the present disclosure provides a system for analyzing nucleic acid molecules from a biological sample of a subject of an organism, the system comprising: a database that stores a plurality of sequence reads generated upon sequencing said nucleic acid molecules; and one or more computer processors operatively coupled to said database, wherein said one or more computer processors are individually or collectively programmed to execute instructions for: (a) identifying a first genomic region in a reference genome of the organism with a mappability score below a threshold and a second genomic region in the reference genome of the subject with a mappability score above the threshold, wherein the second genomic region is adjacent to one end of the first genomic region; (b) performing local de novo assembly of a first subset of the sequence reads that align to the first genomic region and a second subset of the sequence reads that align to the second genomic region, thereby generating contigs, wherein at least one of the contigs extends over a portion of the first genomic region and a portion of the second genomic region; and (c) recovering sequence data corresponding to the contigs within the first genomic region, wherein the recovered genomic sequence data comprise at least a portion of the first subset of sequence read.

In some embodiments, the general instructions further comprise instructions for identifying a third genomic region in the reference genome having a mappability score above the threshold, wherein the third genomic region is located on the other end of the first genomic region, wherein the contigs are generated by local de novo assembly of the first subset, the second subset, and the third subset of the sequence reads, and wherein at least one of the contigs extends over a portion of the first genomic region and a portion of the third genomic region.

In some embodiments, the reference genome comprises a plurality of genomic regions, and the general instructions further comprises instructions for: (d) repeating steps (a)-(c) for each of the genomic regions having a mappability score below the threshold, thereby recovering portions of the sequence data from all of the genomic regions having mappability scores below the threshold.

In some embodiments, the general instructions further comprise instructions for combining the recovered sequence data from (d) with sequence data from genomic regions that have mappability scores above the threshold.

In some embodiments, the general instructions further comprise instructions for: normalizing the combined sequence data using a covariate of GC content.

In some embodiments, the general instructions further comprise instructions for performing statistical smoothing on the combined sequence data.

In some embodiments, the local de novo assembly is performed using an algorithm selected from the group consisting of a greedy algorithm assembler, graph method assembler, string graph assembler, De Bruijn graph assembler, Spades, Ray, ABySS, ALLPATHS-LG, and Trinity. In some embodiments, the local de novo assembly comprises creation of a scaffold comprising the contigs, and wherein the recovered sequence data align to the scaffold. In some embodiments, the sequence reads comprise paired-end sequence reads, and the scaffold is created by ordering the contigs based on paired-end information of the paired-end sequence reads.

In some embodiments, the recovered sequence data comprise sequence reads that align uniquely to the contigs within the first genomic region. In some embodiments, the recovered sequence data further comprise sequence reads that align to genomic regions of the reference genome other than the first genomic region.

In some embodiments, the general instructions further comprise instructions for segmenting the combined sequence data to identify a chromosomal aberration. In some embodiments, the combined sequence data is segmented into a copy number state, the copy number state selected from the group consisting of a copy number loss state, a copy number gain state, and a copy number normal state. In some embodiments, the copy number state comprises the copy number normal state, and wherein a variability of the copy number normal state is determined using at least one of a healthy reference sample and a tumor reference sample. In some embodiments, the instructions for the segmenting comprise instructions for using a Markov model statistical analysis. In some embodiments, the Markov model is a Hidden Markov model. In some embodiments, the Hidden Markov model comprises an ergodic model.

In some embodiments, said chromosomal aberration comprises a copy number aberration. In some embodiments, the copy number aberration is from a tumor. In some embodiments, said chromosomal aberration is identified in the absence of identifying one or more single nucleotide polymorphisms in said nucleic acid molecules.

In some embodiments, the instructions for the identifying the first genomic region and the second genomic region comprise instructions for comparing the mappability score of the first genomic region against the threshold and the mappability score of the second genomic region against the threshold. In some embodiments, the mappability score of the first genomic region and the second genomic region is determined according to the following: partitioning the first genomic region into a first plurality of partitioned sequences and the second genomic region into a second plurality of partitioned sequences, and determining the mappability score of the first genomic region based, at least in part, on a first percentage of the first plurality of partitioned sequences that uniquely align to the first genomic region, and the mappability score of the second genomic region based, at least in part, on a second percentage of the second plurality of partitioned sequences that uniquely align to the second genomic region.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

FIGS. 3A-C show an exemplary 3-step method of the present disclosure.

DETAILED DESCRIPTION

Overview

Figure 1:
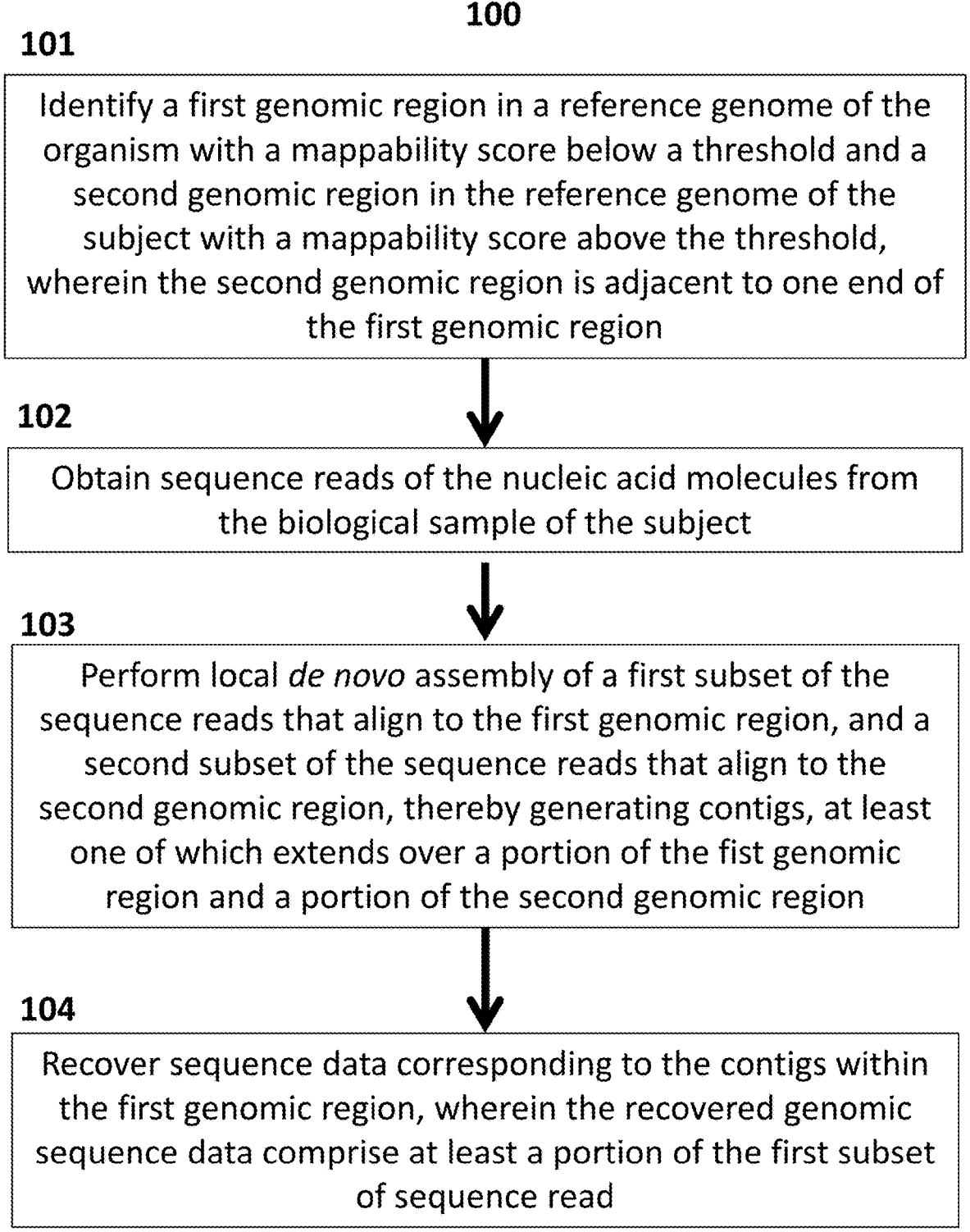
FIG. 1 shows a flowchart of an exemplary method of the present disclosure.

Provided herein are methods for analyzing nucleic acid molecules, e.g., cell-free nucleic acid molecules, from a biological sample of a subject (see, e.g., FIG. 1). The methods (100) can involve identifying a first genomic region in a reference genome, e.g., a reference genome of the subject, or a reference genome of a species related to the subject (for instance, human reference genome relative to chimpanzee, or vice versa), that has a mappability below a threshold and a second genomic region of the reference genome that is adjacent to one end of the first genomic region and has a mappability above the threshold (101). The methods can comprise obtaining sequence reads of nucleic acid molecules, e.g., cell-free nucleic acid molecules from the biological sample of the subject (102). The methods can comprise performing local de novo (LDN) assembly of a first subset of the sequence reads that align to the first genomic region, and a second subset of the sequence reads that align to the second genomic region, thereby generating contigs, at least one of which extends over a portion of the first genomic region and a portion of the second genomic region (103). Optionally, the LDN assembly can generate a scaffold that comprises the contigs. The methods can comprise recovering sequence data corresponding to the contigs within the first genomic region, the recovered genomic sequence data comprise at least a portion of the first subset of sequence read (104).

In some cases, the methods further comprise identifying a third genomic region in the reference genome having a mappability score above the threshold, wherein the third genomic region is located on the other end of the first genomic region, wherein the contigs are generated by local de novo assembly of the first subset, the second subset, and the third subset of the sequence reads, and wherein at least one of the contigs extends over a portion of the first genomic region and a portion of the third genomic region.

In some cases, the reference genome comprises a plurality of genomic regions. In some cases, the method further comprises: repeating steps 101, 103, and 104 for each of the genomic regions having a mappability score below the threshold, thereby recovering portions of the sequence data from all of the genomic regions having mappability scores below the threshold. In some cases, the methods further comprise combining the recovered sequence data, e.g., recovered sequence data from all genomic regions with mappability scores below the threshold, with sequence data from genomic regions that have mappability scores above the threshold.

By combining mappability analysis and LDN assembly, the methods provided herein can improve genomic coverage for sequencing analysis. In some cases, the methods can improve genomic coverage with no or little sacrifice of the read quality, e.g., increase of noise in the sequencing analysis, e.g., introduction of noisy sequence reads to the sequencing analysis, or increase in coefficient variance of the pool of sequence reads used for the analysis.

In some cases, when analyzing sequencing reads, mappability analysis is introduced to exclude genomic regions that do not meet a mappability threshold. In some cases, a reference genome can be broken down into a plurality of genomic regions (bins), and each bin is analyzed for its mappability. A mappability threshold can be determined and compared against the mappability value of each bin of the reference genome. In some cases, genomic regions having mappability below the threshold are excluded for follow-on analysis of the sequencing data, e.g., sequence reads that align to genomic regions having mappability below the threshold are excluded for further analysis.

Without wishing to be bound to a certain theory, sequence reads that align to genomic regions of lower mappability can be associated with higher noise, as compared to genomic regions of higher mappability. In some cases, by setting a relatively high mappability threshold, one can expect to have a relatively low noise level or relatively more stabilized noise distribution across the sequence reads subject for further analysis.

In some cases, the application of mappability analysis and exclusion of genomic regions having low mappability can result in loss of genomic information, for instance, sequence information from the excluded genomic regions. In some cases, the lost genomic information can be useful for the purpose of the sequencing analysis, and it can be beneficial to resurrect as much as possible meaningful genomic information while performing sequencing analysis. For instance, as demonstrated in Example 3 and FIG. 5, in human genome, lower mappability can be mostly at telomeres or centromeres, and there can be non-contiguous or focal lower mappability regions outside telomeres and centromeres. In some cases, copy number changes in the neighborhood of telomeres and centromeres and copy number changes of more focal nature cannot be characterized if genomic regions of lower mappability are excluded for copy number estimation. Focal copy number aberrations are implicated in cancer, and can be used as a hallmark of cancer, e.g., ovarian cancer (such as described in Zhang et al., BMC Bioinformatics, 2016; 17: 222), breast cancer (such as described in Sun et al., BioMed Research International, vol. 2015, Article ID 901303, 11 pages, 2015), and osteosarcoma (such as described in Both et al., PLoS ONE 9(12): e115835). Therefore, resurrecting lost genomic information from low mappability genomic regions can be useful for accurate sequence analysis of nucleic acid molecules from a biological sample of a subject, e.g., determination of copy number aberrations of the nucleic acid molecules. In some cases, resurrecting lost genomic information from low mappability genomic regions can be useful for diagnosing, monitoring, or prognosticating a cancer in the subject based on the analysis of the nucleic acid molecules from the subject.

Figure 6:
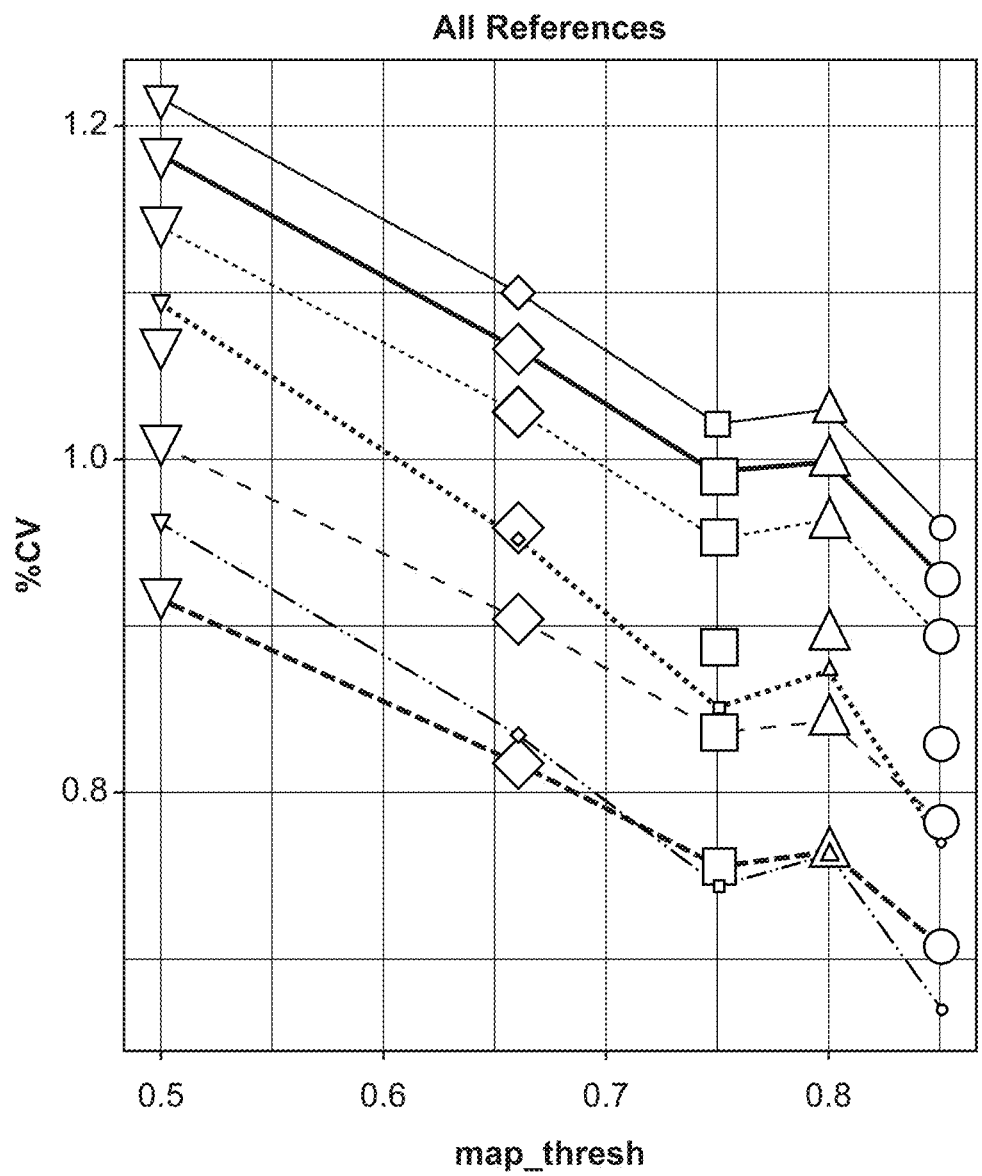
FIG. 6 illustrates exemplary correlation between mappability threshold, sequence read depth, and noise level in copy number analysis without local de novo assembly as described herein.
Figure 7:
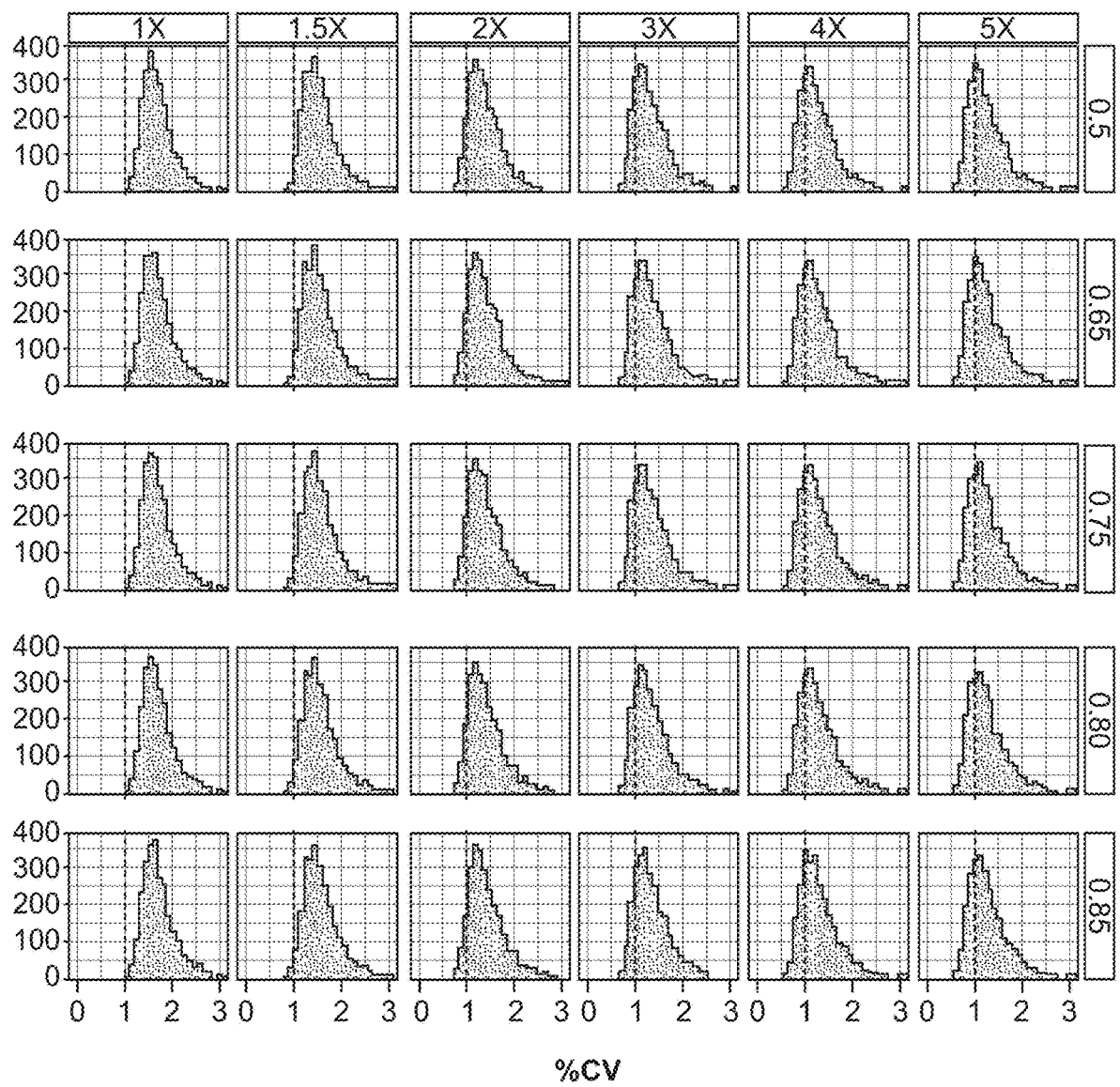
FIG. 7 shows noise distribution in exemplary copy number analyses without local de novo assembly as described herein.

Recovery of the lost genomic information due to mappability analysis can be challenging. One method to improve genomic coverage can be lowering the mappability threshold, thereby reducing the size of the genomic regions to be excluded from the analysis. However, in some cases, such an approach can suffer from increased noise in the sequence reads, which can lead to reduced quality of sequencing analysis. FIGS. 6 and 7 demonstrate an exemplary scenario where noise level reversely correlates with the mappability threshold applied during copy number estimation from a pool of sequencing reads (details described in Example 4 below).

In some cases, the high noise introduced in sequencing analysis can be remedied by increasing sequencing depth. For instance, sequencing depth at 5× can generate sequencing data with lower noise level than sequencing data generated from sequencing at 1× depth. However, increasing sequencing depth can render the sequencing less economically viable, increasing both time and monetary cost.

The methods provided herein can improve genomic coverage while maintaining relative low noise level. Without wishing to be bound by a certain theory, the methods provided herein, in some cases, do not significantly affect the noise level by not lowering the mappability threshold that is applied to exclude some of the genomic regions for follow-on analysis. Rather, in some cases, the methods provided herein comprise performing local de novo assembly in the genomic regions with mappability below the threshold. LDN assembly can generate contigs formed by assembling overlapping raw sequence reads (e.g., all sequence reads including reads that map to different genomic loci). After LDN assembly, sequence reads that align to the contigs can be recovered for further analysis together with other sequence reads that map to genomic regions with mappability above the threshold.

The present disclosure provides methods for determining one or more chromosomal aberrations in a subject using a biological sample obtained from the subject. The methods can make use of methods that improve sequence read mappability to a reference genome described herein. The methods disclosed herein can employ statistical modeling (e.g., Markov modeling, e.g., Hidden Markov Modeling) to detect one or more chromosomal aberrations, such as copy number variations, in the subject.

The methods and systems disclosed herein can solve the problem of current genomic binning based methods by determining chromosomal aberrations via a Markov model statistical analysis. The methods described herein can be improvements over current methods for determining the presence or absence of copy number variations because commonly used binning methods are not required. Genomic binning (or windowing) can be a simplistic approach that can introduce many potential artifacts which can adversely impact the sensitivity and specificity of detection. Imposition of artificial boundaries conflated with genome-wide variation in sequence mappability can be a significant source of one such error.

Disclosed herein, in some aspects, are systems for analyzing a plurality of cell-free nucleic acids molecules from a biological sample of a subject for a chromosomal aberration in said subject, comprising: a database that stores a plurality of sequence reads generated upon sequencing said plurality of cell-free nucleic acid molecules; and one or more computer processors operatively coupled to said database, wherein said one or more computer processors are individual or collectively programmed to: align said plurality of sequence reads to a reference genome; determine a mappability for each of a plurality of genomic regions of said reference genome, and for each genomic region of said plurality of genomic regions, use said mappability to determine a subset of genomic regions of said plurality of genomic regions that does not meet a threshold value; perform de novo sequence assembly in one or more of said subset of genomic regions; determine genomic sequence data, e.g., combined sequence data, corresponding to said subject based at least in part on said aligned plurality of sequence reads and said de novo sequence assembly; and segment said genomic sequence data, e.g., the combined sequence data, using a Markov model statistical analysis to identify said chromosomal aberration in said subject.

Definitions

The term "chromosomal aberration," as used herein, can refer to any significant deviation in a quantity of a chromosomal region as compared to a reference quantity. A chromosomal aberration can refer to a deviation in the quantity of one or more nucleic acids or nucleic acid fragments corresponding to a chromosomal region as compared to a reference quantity. A sequence imbalance can include chromosome dosage imbalance, allelic imbalance, mutation dosage imbalance, copy number aberration, insertions, deletions, duplications, translocations, inversions, rings, haplotype dosage imbalance, and other similar imbalances. As an example, an allelic imbalance can occur when a tumor has one allele of a gene deleted or one allele of a gene amplified or differential amplification of the two alleles in its genome, thereby creating an imbalance at a particular locus in the sample. As another example, a patient can have an inherited mutation in a tumor suppressor gene. The patient can then go on to develop a tumor in which the non-mutated allele of the tumor suppressor gene is deleted. Thus, within the tumor, there can be mutation dosage imbalance. The tumor can release its deoxyribonucleic acid (DNA) and/or ribonucleic acid (RNA). For example, when the tumor releases its DNA into the plasma of the patient, the tumor DNA can be mixed in with the constitutional DNA (e.g., from normal cells) of the patient in the plasma. Through the use of methods described herein, mutational dosage imbalance of this DNA mixture in the plasma can be detected.

Genetic and chromosomal aberrations including aberrations in copy number, for example, allelic imbalances, chromosomal copy number changes, such as amplifications, deletions, aneuploidy, loss of heterozygosity, and microsatellite instability can be found to be associated with a disease state, for example, cancer. Alterations in chromosomal copy number and loss of heterozygosity (LOH) can be forms of genetic changes that can signal the activation of oncogenes and inactivation of tumor suppressor genes (anti-oncogenes). Variations in the form of copy number polymorphisms (CNP) can also occur in normal individuals. Identification of the loci implicated in these aberrations can generate anchor points which facilitate oncogenomics and toxicogenomics studies. Subsequently, the shared LOH and aberrant CNP regions can be used to partition the transcriptome data and track the differential transcript expression in the affected genomic segments. Locating and exploring such alteration events can be used to understand the cause and progression of disease.

The term "healthy" can refer to a subject possessing good health. Such a subject can demonstrate an absence of any malignant or non-malignant disease. A "healthy individual" can have other diseases or conditions, unrelated to the condition being assayed that can normally not be considered "healthy".

The term "sample", "biological sample" or "subject sample," as used herein, can refer to any tissue or material derived from a living or dead subject. A biological sample can be a cell-free sample. A biological sample can comprise a nucleic acid (e.g., DNA or RNA), a derivative thereof, or a fragment thereof. The nucleic acid in the sample can be a cell-free nucleic acid. A sample can be a liquid sample or a solid sample (e.g., a cell or tissue sample). The biological sample can be a bodily fluid, such as blood (e.g., whole blood), plasma, serum, urine, vaginal fluid, fluid from a hydrocele (e.g., of the testis), vaginal flushing fluids, pleural fluid, ascitic fluid, cerebrospinal fluid, saliva, sweat, tears, sputum, bronchoalveolar lavage fluid, discharge fluid from the nipple, aspiration fluid from different parts of the body (e.g., thyroid, breast), etc. Stool samples can also be used. In various embodiments, the majority of DNA in a biological sample that has been enriched for cell-free DNA (e.g., a plasma sample obtained via a centrifugation protocol) can be cell-free (e.g., greater than 50%, 60%, 70%, 80%, 90%, 95%, or 99% of the DNA can be cell-free). The biological sample can be treated to physically disrupt tissue or cell structure (e.g., centrifugation and/or cell lysis), thus releasing intracellular components into a solution which can further contain enzymes, buffers, salts, detergents, and the like which are used to prepare the sample for analysis.

The term "cancer" or "tumor," as used herein, can refer to an abnormal mass of tissue in which the growth of the mass can surpass and cannot be coordinated with the growth of normal tissue. A cancer or tumor can be "benign" or "malignant" depending on the following characteristics: degree of cellular differentiation including morphology and functionality, rate of growth, local invasion and metastasis. A "benign" tumor can be well differentiated, and can have characteristically slower growth than a malignant tumor and remain localized to the site of origin. In addition, a benign tumor does not have the capacity to infiltrate, invade or metastasize to distant sites. A "malignant" tumor can be poorly differentiated (anaplasia), have rapid growth accompanied by progressive infiltration, invasion, and destruction of the surrounding tissue. Furthermore, a malignant tumor can have the capacity to metastasize to distant sites.

The term "sequence read" (or "sequencing read"), as used herein, can refer to a string of nucleotides sequenced or otherwise identified from any part or all of a nucleic acid molecule. For example, a sequence read can be a short string of nucleotides (e.g., 20-150) sequenced from a nucleic acid fragment, a short string of nucleotides at one or both ends of a nucleic acid fragment, or the sequencing of the entire nucleic acid fragment that exists in the biological sample. A sequence read can be obtained in a variety of ways, e.g., using sequencing techniques. Additional sequence information can be obtained using probes, e.g., in hybridization arrays or capture probes, or amplification techniques, such as the polymerase chain reaction (PCR) or linear amplification using a single primer or isothermal amplification.

Subjects

The subject can have, or be suspected of having, any type of cancer or tumor. The cancer cancer can be adrenal cancer, anal cancer, basal cell carcinoma, bile duct cancer, bladder cancer, cancer of the blood, bone cancer, a brain tumor, breast cancer, bronchus cancer, cancer of the cardiovascular system, cervical cancer, colon cancer, colorectal cancer, cancer of the digestive system, cancer of the endocrine system, endometrial cancer, esophageal cancer, eye cancer, gallbladder cancer, a gastrointestinal tumor, hepatocellular carcinoma, kidney cancer, hematopoietic malignancy, laryngeal cancer, leukemia, liver cancer, lung cancer, lymphoma, melanoma, mesothelioma, cancer of the muscular system, Myelodysplastic Syndrome (MDS), myeloma, nasal cavity cancer, nasopharyngeal cancer, cancer of the nervous system, cancer of the lymphatic system, oral cancer, oropharyngeal cancer, osteosarcoma, ovarian cancer, pancreatic cancer, penile cancer, pituitary tumors, prostate cancer, rectal cancer, renal pelvis cancer, cancer of the reproductive system, cancer of the respiratory system, sarcoma, salivary gland cancer, skeletal system cancer, skin cancer, small intestine cancer, stomach cancer, testicular cancer, throat cancer, thymus cancer, thyroid cancer, a tumor, cancer of the urinary system, uterine cancer, vaginal cancer, or vulvar cancer.

The cancer can be a lymphoma. The lymphoma can be any type of lymphoma including B-cell lymphoma (e.g., diffuse large B-cell lymphoma, follicular lymphoma, small lymphocytic lymphoma, mantle cell lymphoma, marginal zone B-cell lymphoma, Burkitt lymphoma, lymphoplasmacytic lymphoma, hairy cell leukemia, or primary central nervous system lymphoma) or a T-cell lymphoma (e.g., precursor T-lymphoblastic lymphoma, or peripheral T-cell lymphoma).

The cancer can be a leukemia. The leukemia can be any type of leukemia, e.g., acute leukemia or chronic leukemia. The leukemia can be acute myeloid leukemia, chronic myeloid leukemia, acute lymphocytic leukemia, acute undifferentiated leukemia, or chronic lymphocytic leukemia. In some cases, the cancer subject does not have a particular type of cancer. For example, in some instances, the subject can have a cancer that is not breast cancer.

The cancer can be a solid tumor. In some cases, the cancer is not a solid tumor. The cancer can be a primary cancer (e.g., a cancer that is named after the part of the body where it first started to grow) or a secondary or metastatic cancer (e.g., a cancer that has originated from another part of the body).

The subject can be at risk of cancer or be at risk because of a particular condition such as a pre-cancerous condition. The pre-cancerous condition can be actinic keratosis, Barrett's esophagus, atrophic gastritis, ductal carcinoma in situ, dyskeratosis congenita, sideropenic dysphagia, lichen planus, oral submucous fibrosis, solar elastosis, cervical dysplasia, leukoplakia, or erythroplakia. In some cases, the subject can be at risk of cancer because of cell or tissue dysplasia (e.g., an abnormal change in cell number, abnormal change in cell shape, abnormal change in cell size, or abnormal change in cell pigmentation). The subject that is at risk of cancer can be a subject that was exposed to a carcinogenic agent. The subject can be exposed to known or probable carcinogens (e.g., acetyl aldehyde, asbestos, or tobacco products), or exposed to ionizing radiation (e.g., gamma radiation, beta-radiation, X-radiation, or ultraviolet radiation). In some cases, the subject is at risk because of a family history of cancer.

In some aspects, a method of the present disclosure can detect a tumor or cancer in a subject, wherein the tumor or cancer has a geographic pattern of disease. In an example, a subject can have an Epstein-Barr virus (EBV)-related cancer (e.g., nasopharyngeal cancer), which can be prevalent in South China (e.g., Hong Kong SAR). In another example, subject can have an HPV-related cancer (e.g., oropharyngeal cancer), which can be prevalent in the United States and Western Europe. In yet another example, a subject can have a Human T-lymphotrophic virus-1 (HTLV-1)-related cancer (e.g., adult T-cell leukemia/lymphoma), which can be prevalent in southern Japan, the Caribbean, central Africa, parts of South America, and in some immigrant groups in the southeastern United States.

The cancer can be caused by a virus (e.g., an oncovirus), e.g., a DNA or RNA virus. The subject can have a cancer, and the cancer can be detectable using viral DNA. A subject can have cancer, and the cancer can be detectable using tumor-derived viral DNA. A subject can have a cancer, and the cancer can be detectable using tumor-derived viral DNA, or a fragment thereof, in cell-free sample obtained from the subject (e.g., a blood sample, a plasma sample, or a serum sample). A person having skill in the art will appreciate that a virus can have multiple viral strains (e.g., related viruses that can differ in their genetic makeup), which are included within the scope of the embodiments of the present application. For example, a subject can have oral, oropharyngeal, cervical cancer, penile, anal, vaginal, or vulvar cancer caused by (or associated with) infection by a Human papilloma virus (HPV), which can include more than 150 related viruses. Infection with the Epstein-Barr virus (EBV) can also increase a subject's risk of developing nasal cancer, nasopharyngeal cancer, lymphomas (e.g., Burkitt lymphoma or Hodgkin lymphoma), or stomach cancer. In yet another example, infection with the Hepatitis B virus (HBV) or Hepatitis C virus can cause chronic infections, which can increase a subject's chance of developing liver cancer. Non-limiting examples of viruses that can cause, or be associated with, cancer in a subject include HPV, EBV, HBV, HCV, Human immunodeficiency virus (e.g., associated with Kaposi sarcoma, cervical cancer, non-Hodgkin lymphoma, anal cancer, Hodgkin disease, lung cancer, oral cancer, oropharyngeal cancer, skin cancer, and liver cancer), human herpes virus 8 (e.g., associated with Kaposi sarcoma, blood cancer, primary effusion lymphoma, and Castleman disease), Human T-lymphotrophic virus-1 (e.g., associated with lymphocytic leukemia, non-Hodgkin lymphoma, and adult T-cell leukemia/lymphoma), and Merkel cell polyomavirus (e.g., associated with skin cancers such as Merkel cell carcinoma). A non-human subject (e.g., a primate) can have cancer, and the cancer can be detectable using tumor-derived viral DNA. For example, infection with Simian virus 40 (SV40) can increase a subject's risk of developing mesothelioma, brain tumor, bone cancer, and lymphoma.

The subject can be of any age. The subject can be an adult, infant, or child. In some cases, the subject is 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 years old, or within a range therein (e.g., between 2 and 20 years old, between 20 and 40 years old, or between 40 and 90 years old). Furthermore, the subject can be male or female.

Any of the methods disclosed herein can also be performed on a non-human subject, such as a laboratory or farm animal, or a cellular sample derived from an organism disclosed herein. Non-limiting examples of a non-human subject include a dog, a goat, a guinea pig, a hamster, a mouse, a pig, a non-human primate (e.g., a gorilla, an ape, an orangutan, a lemur, or a baboon), a rat, a sheep, a cow, or a zebrafish.

Methods for Improving Genomic Coverage and Determination of Chromosomal Aberrations In an aspect, the present disclosure provides a method for the determination of a presence or absence of a chromosomal aberration in a biological sample of a subject. The chromosomal aberration can comprise a copy number aberration. The copy number aberration can be from a tumor. The methods can comprise analyzing a plurality of nucleic acid molecules, e.g., cell-free nucleic acids molecules, from the biological sample. The methods can make use of improved methods for genomic coverage.

FIG. 1 shows an exemplary method for recovering sequence data from genomic regions having low mappability (100). In some embodiments, regions of low mappability can be identified for a reference genome (101). As disclosed herein, a reference genome is associated with a specific organism, but not a particular subject of the organism. For example, GRCh37, the Genome Reference Consortium human genome (build 37) is derived from thirteen anonymous volunteers from Buffalo, N.Y. A variety of methods can be used to compute mappability of regions within a reference genome. For example, the genome database hosted at University of California, Santa Cruz (UCSC) offers a platform for computing mappability scores associated with different genomic regions. As multiple reference genome can be assembled for the same organism, mappability can be computed for each reference genome. As disclosed here, a predetermined threshold will be used to identify genomic regions of for further processing based on their respective mappability scores. In some embodiments, a first genome region having a mappability score below the predetermined threshold is selected. In some embodiments, the first genome region has at one end a neighboring or immediately adjust genomic region that has a mappability score above the predetermined threshold value. In some embodiments, the first genome region has at each end a neighboring or immediately adjust genomic region that has a mappability score above the predetermined threshold value. As such that the genomic region of low mappability is flanked by two genomic regions that each have a mappability score above the predetermined threshold. At step 102, sequence reads are obtained of nucleic acid molecules from a biological sample from a subject. The subject is of the same organism as the reference genome. As disclosed herein, the biological sample can comprise blood, whole blood, plasma, serum, urine, cerebrospinal fluid, fecal, saliva, sweat, tears, pleural fluid, pericardial fluid, or peritoneal fluid of the subject. Sequence reads can be obtained from whole genome sequencing, whole genome bisulfite sequence, or targeted sequencing. At step 103, sequence reads that align to the first genomic region (a low mappability region) form a first subset of sequence reads. Sequence reads that align to one or both high mappability genomic regions that flank the first genomic region form a second subset of sequence reads. Local de no assembly is subsequently performed using the first and second subsets of sequence reads to construct sequence contigs. As disclosed herein, at least one contig extends across the borders between the low mappability genomic region (e.g., first genomic region) and the high mappability genomic region (e.g., second genomic region). In some embodiments, when the low mappability first genomic region is flanked on both ends with a high mappability region (e.g., a second genomic region and a third genomic region), there are at least one contig that extends across the boundary between the first and second genomic regions and at least another contig that extends across the boundary between the first and third genomic regions. At step 104, sequence data corresponding to the contigs within the first genomic region are recovered and subject to further analysis. Such sequence data would be rejected by conventional method because they belong to a genomic region that falls below the predetermined threshold. The method is advantageous over a method of simply lowering the mappability threshold value, which would lead to inclusion of noisy data.

Nucleic Acids

Nucleic acids used in the methods provided herein can be also be referred to as polynucleotides, which can refer to at least two nucleotides covalently linked together. A nucleic acid described herein can contain phosphodiester bonds, although in some cases, as outlined below (for example in the construction of primers and probes such as label probes), nucleic acid analogs are included that can have alternate backbones, comprising, for example, phosphoramide (Beaucage et al., Tetrahedron 49(10):1925 (1993) and references therein; Letsinger, J. Org. Chem. 35:3800 (1970); Sprinzl et al., Eur. J. Biochem. 81:579 (1977); Letsinger et al., Nucl. Acids Res. 14:3487 (1986); Sawai et al, Chem. Lett. 805 (1984), Letsinger et al., J. Am. Chem. Soc. 110:4470 (1988); and Pauwels et al., Chemica Scripta 26:141 91986)), phosphorothioate (Mag et al., Nucleic Acids Res. 19:1437 (1991); and U.S. Pat. No. 5,644,048), phosphorodithioate (Briu et al., J. Am. Chem. Soc. 111:2321 (1989), O-methylphosphoroamidite linkages (see Eckstein, Oligonucleotides and Analogues: A Practical Approach, Oxford University Press), and peptide nucleic acid (also referred to herein as "PNA") backbones and linkages (see Egholm, J. Am. Chem. Soc. 114:1895 (1992); Meier et al., Chem. Int. Ed. Engl. 31:1008 (1992); Nielsen, Nature, 365:566 (1993); Carlsson et al., Nature 380:207 (1996), all of which are incorporated by reference). Other analog nucleic acids include those with bicyclic structures including locked nucleic acids (also referred to herein as "LNA"), Koshkin et al., J. Am. Chem. Soc. 120.13252 3 (1998); positive backbones (Denpcy et al., Proc. Natl. Acad. Sci. USA 92:6097 (1995); non-ionic backbones (U.S. Pat. Nos. 5,386,023, 5,637,684, 5,602,240, 5,216,141 and 4,469,863; Kiedrowski et al., Angew. Chem. Intl. Ed. English 30:423 (1991); Letsinger et al., J. Am. Chem. Soc. 110:4470 (1988); Letsinger et al., Nucleoside & Nucleotide 13:1597 (1994); Chapters 2 and 3, ASC Symposium Series 580, "Carbohydrate Modifications in Antisense Research", Ed. Y. S. Sanghui and P. Dan Cook; Mesmaeker et al., Bioorganic & Medicinal Chem. Lett. 4:395 (1994); Jeffs et al., J. Biomolecular NMR 34:17 (1994); Tetrahedron Lett. 37:743 (1996)) and non-ribose backbones, including those described in U.S. Pat. Nos. 5.235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within the definition of nucleic acids (see Jenkins et al., Chem. Soc. Rev. (1995) pp 169 176). Several nucleic acid analogs are described in Rawls, C & E News Jun. 2, 1997 page 35. "Locked nucleic acids" can also be included within the definition of nucleic acid analogs. LNAs can be a class of nucleic acid analogues in which the ribose ring is "locked" by a methylene bridge connecting the 2'-0 atom with the 4'-C atom. All of these references are hereby expressly incorporated by reference. These modifications of the ribose-phosphate backbone can be done to increase the stability and half-life of such molecules in physiological environments. For example, PNA:DNA and LNA-DNA hybrids can exhibit higher stability and thus can be used in some embodiments. The target nucleic acids can be single stranded or double stranded, as specified, or contain portions of both double stranded or single stranded sequence. Depending on the application, the nucleic acids can be DNA (e.g., genomic DNA, mitochondrial DNA, and cDNA), RNA (e.g., mRNA and rRNA) or a hybrid, where the nucleic acid contains any combination of deoxyribo- and ribo-nucleotides, and any combination of bases, including uracil, adenine, thymine, cytosine, guanine, inosine, xathanine hypoxathanine, isocytosine, isoguanine, etc. The nucleic acids can be DNA, RNA, mitochondrial DNA, genomic DNA, mRNA, siRNA, miRNA, cRNA, single-stranded DNA, double-stranded DNA, single-stranded RNA, double-stranded RNA, tRNA, rRNA, cDNA, cell-free DNA, cell-free RNA, circulating DNA, circulating RNA, etc.

The analysis of the nucleic acid molecules, e.g., cell-free nucleic acid molecules, can comprise amplifying the nucleic acid molecules, e.g., cell-free nucleic acid molecules. A nucleic acid can be flanked on one end by a first adapter and flanked on the other end by a second adapter. A nucleic acid can be flanked on one end by a first adapter and flanked on the other end by a second adapter can be analyzed via amplification and/or sequencing. Analyzing a nucleic acid can comprise amplifying the nucleic acid, sequencing the nucleic acid, detecting epigenetic markers (e.g., methylation, hydroxymethylation), or any combination thereof. Amplification of the nucleic acid can refer to a process by which one or more nucleic acids can be copied, thereby generating an amount of copies of the nucleic acid that can be multiple orders of magnitude greater than the starting number of nucleic acids. For example, amplification can be used in any of the methods disclosed herein for increasing the number of copies of the nucleic acid in the sample. Amplification of a nucleic acid can be performed by a variety of techniques. The amplification technique can be any one or more of reverse transcription-PCR, real-time PCR, quantitative real-time PCR, digital PCR (dPCR), digital emulsion PCR (dePCR), clonal PCR, amplified fragment length polymorphism PCR (AFLP PCR), allele specific PCR, assembly PCR, asymmetric PCR (in which a great excess of primers for a chosen strand can be used), colony PCR, helicase-dependent amplification (HDA), Hot Start PCR, inverse PCR (IPCR), in situ PCR, long PCR (extension of DNA greater than about 5 kilobases), multiplex PCR, nested PCR (uses more than one pair of primers), single-cell PCR, touchdown PCR, loop-mediated isothermal PCR (LAMP), recombinase polymerase amplification (RPA), and nucleic acid sequence based amplification (NASBA).

Other amplification methods that can be used in the methods provided herein include LCR (ligase chain reaction) which can utilize DNA ligase and a probe comprising two halves of a DNA segment that is complementary to the sequence of the DNA to be amplified; enzyme QB replicase and an RNA sequence template attached to a probe complementary to the DNA to be copied, which can be used to make a DNA template for exponential production of complementary RNA; strand displacement amplification (SDA); multiple displacement amplification; ramification amplification; Qβ replicase amplification (QβRA); self-sustained replication (3SR); Branch DNA Amplification; Rolling Circle Amplification; Circle to Circle Amplification; single primer isothermal amplification (SPIA) amplification; Target Amplification by Capture and Ligation (TACL) amplification; and RACE amplification.

One technique that can be used for nucleic acid amplification is PCR. PCR can be a process of nucleic acid amplification that involves an enzymatic chain reaction for preparing exponential quantities of a specific nucleic acid sequence. PCR can involve cycling the temperature of the reaction to denature nucleic acids into single strands, anneal primers to regions of the nucleic acid that are complementary to the primer, and copy the denatured nucleic acid by extension or elongation from the primer using an enzyme and nucleotides. This can result in newly synthesized extension products. These newly synthesized sequences can become templates for the primers, and repeated cycles of denaturing, primer annealing, and extension can result in exponential accumulation of the specific sequence being amplified. The extension product of the chain reaction can be a discrete nucleic acid duplex with a terminus corresponding to the ends of the specific primers employed. PCR can require a small amount of starting nucleic acid material to initiate the chain reaction, and the technique can be useful for assaying samples with low nucleic acid content.

Analyzing a nucleic acid can involve the use of a primer or probe. A primer can refer to a short synthetic nucleic acid molecule whose sequence matches a region flanking the target nucleic acid that is to be amplified. A primer can be between 10 and 50 nucleotides in length, inclusive. A primer can be less than 10 nucleotides in length. A primer can be greater than 50 nucleotides in length. Primers can comprise any number of adenine (A), thymine (T), guanine (G), cytosine (C), or uracil (U) nucleotides. The type, number and arrangement of each of the nucleotides in the primer can affect the affinity between the primer and a primer binding site and/or the temperature at which the primer can bind to a primer binding site. For example, the guanine-cytosine (e.g., GC content) can be the percentage of nitrogenous bases on a DNA molecule that are either guanine or cytosine, and can be used to predict the temperature at which the primer anneals to a nucleic acid. The GC-content of the primer can be about 60%. The GC-content of the primer can be between 50% and 60%, inclusive. The GC content can be at least 10%, at least 20%, at least 30%, at least 40%, at least 50%, at least 60%, at least 70%, at least 80%, or at least 90%. A primer can be a universal primer. A universal primer can contain a unique amplification or sequencing priming region that can be, for example, about 5, 7, 10, 13, 15, 17, 20, 22, or 25 nucleotides in length, and can be present on each polynucleotide of a plurality of polynucleotides to be amplified. A universal primer can be used to amplify multiple polynucleotides simultaneously, in a single reaction, and/or with similar amplification efficiencies. The primer can be conjugated with another molecule (e.g., a ribozyme), thereby allowing the primer to bind to a nucleic acid and self-cleave at a designated endonuclease recognition site. The attached molecule can be temperature sensitive and/or pH sensitive. For example, analyzing a nucleic acid can comprise PCR amplification of the nucleic acid, wherein a ribozyme-conjugated primer can be used to bind to the nucleic acid to allow repeated replication until the temperature is changed (e.g., increased or decreased) and the molecule is activated, thereby terminating replication.

The nucleic acid molecules, e.g., cell-free nucleic acid molecules, can be amplified by whole genome amplification. The products of the whole genome amplification can be used for downstream analysis; e.g., sequencing, e.g., next-generation sequencing.

The nucleic acid molecules, e.g., cell-free nucleic acid molecules, can be enriched by a targeted method. The number of nucleic acid molecule targets that can be enriched can be about 1, about 10, about 100, about 1000, about 10,000, about 100,000, about 1,000,000, or about 10,00,000. The number of nucleic acid molecule targets that can enriched can be greater than 1, greater than 10, greater than 100, greater than 1000, greater than 10,000, greater than 100,000, greater than 1,000,000, or greater than 10,000,000. Targets that are enriched can be used for downstream applications, e.g., sequencing, e.g., next-generation sequencing.

The one or more targets can be enriched using one or more capture probes, e.g., using SURESELECT Target Enrichment from AGILENT TECHNOLOGIES. Nucleic acid, e.g., DNA, e.g., genomic DNA, can be fragmented, e.g., by sonication. The one or more targets can be enriched using one or more probes, e.g., one or more cRNA probes, of about 10 to about 200 bases, about 20 to about 175 bases, about 25 to about 150 bases, or about 120 bases. The one or more probes, e.g., one or more cRNA probes, can be labeled with a label, e.g., biotin, and the label can be bound to a solid support, e.g., a bead (e.g., a magnetic bead), e.g., through a binding moiety, e.g., streptavidin. The solid support, e.g., beads, e.g., magnetic beads, can be captured, e.g., using a magnet. The one or more captured targets can be unbound from the solid support (e.g., by digesting the cRNA probes) amplified, e.g., by PCR, and analyzed, e.g., by sequencing, e.g., next-generation sequencing.

The one or more targets can be enriched, e.g., using HALOPLEX Target Enrichment System from AGILIENT TECHNOLOGIES. Nucleic acid, e.g., DNA, e.g., genomic DNA, can be fragmented, e.g., by restriction enzyme digestion. A probe in the presence of an indexing primer cassette can be used to generate a DNA fragment that is circularized and has one or more indexes incorporated and optionally has one or more sequencing motifs useful for a sequencing platform, e.g., Illumina sequencing. The probe can comprise a label, e.g., biotin, that can be added, e.g., by biotinylation. The label probe can be captured, e.g., using a streptavidin-coated bead (e.g., a magnetic bead). Captured targets can be amplified, e.g., by PCR, and analyzed, e.g., by sequencing, e.g., next-generation sequencing.

The one or more targets can be enriched, e.g., using a transposase, e.g., using NEXTERA tagmentation. The one or more targets can be enriched by addition of adaptors through transposition and then amplifying using primers that anneal to the adaptors by PCR.

The one or more targets can be enriched, e.g., using SEQCAP from ROCHE. Nucleic acid, e.g., DNA, e.g., genomic DNA, can be fragmented, e.g., by sonication. The fragmented DNA can be annealed to capture probes. The capture probes can be labeled. The probes can be bound to solid supports, e.g., magnetic beads coated with streptavidin. The captured targets can be released, amplified, and sequenced.

The one or more targets can be enriched using Single Primer Enrichment Technology (SPET) from NUGEN. Adaptors can be attached to nucleic acid fragments. Primers comprising 3' adaptors can be annealed to target sequence and extended. The extended products can be amplified using primers to adaptor sequences and the amplified products can be analyzed by sequencing, e.g., next-generation sequencing.

Sequencing

Methods provided herein can comprise sequencing the plurality of nucleic acid molecules, e.g., cell-free nucleic acid molecules, to obtain a plurality of sequence reads. Adaptors can be attached to one or more ends of the plurality of nucleic acid molecules, e.g., cell-free nucleic acids. Sequencing the plurality of nucleic acid molecules, e.g., cell-free nucleic acid molecules, can comprise used of adapters attached to one or more ends of the plurality of nucleic acid molecules, e.g., cell-free nucleic acid molecules.

Methods provided herein can comprise labeling the plurality of cell-free nucleic acid molecules with one or more detectable labels, thereby producing a plurality of labeled cell-free nucleic acid molecules. The methods can comprise hybridizing the plurality of labeled cell-free nucleic acid molecules to an array to obtain one or more intensity measurements corresponding to a hybridization of a labeled cell-free nucleic acid molecule of the plurality of labeled cell-free nucleic acid molecules to a probe of said array. Information from microarray studies can be used in the methods provided herein, e.g., with sequencing data, e.g., to identify anchor points for local de novo assembly.

Sequencing the nucleic acid can be performed using various methods. Sequencing can include next generation sequencing, such as sequencing by synthesis or single molecule sequencing. Sequencing the nucleic acid can be performed using chain termination sequencing, hybridization sequencing, 454 sequence (Roche), sequencing using reversible terminator dyes (ILLUMINA sequencing), semiconductor sequencing (THERMOFISHER ION TORRENT), mass spectrophotometry sequencing, massively parallel signature sequencing (MPSS), Maxam-Gilbert sequencing, nanopore sequencing (e.g., using technology from OXFORD NANOPORE or GENIA), single molecule electronic detection sequencing (e.g., measuring tunnel current through nano-electrodes as nucleic acid (DNA/RNA) passes through nanogaps and calculating the current difference; e.g., using QUANTUM SEQUENCING from QUANTUM BIOSYSTEMS), microdroplet single molecule sequence e.g., using pyrophosphorolysis (e.g., using technology from BASE4), polony sequencing, pyrosequencing, shotgun sequencing, single molecule real time (SMRT) sequencing (PACIFIC BIOSCIENCES), GenapSys Gene Electronic Nano-Integrated Ultra-Sensitive (GENIUS) technology from GENAPSYS, GENEREADER from QIAGEN, SOLiD sequencing, or any combination thereof. Sequencing can be initiated from the first end of the nucleic acid comprising the first adapter. The analyzing can comprise sequencing, and the sequencing can be initiated from the second end of the nucleic acid comprising the second adapter.

The sequencing can be whole-genome sequencing (WSG). Whole genome sequencing can include sequencing the subject's chromosomal DNA and mitochondrial DNA. The sequencing can be whole exome sequencing (WES). The sequencing can be targeted sequencing.

The sequence reads used in the methods described herein can be about 10 bases to about 50 bases, about 10 bases to about 100 bases, about 100 bases to about 1,000 bases, about 1,000 to about 10,000 bases, or over 10,000 bases. The sequence reads used in the methods described herein can be at least 10 bases, at least 30 bases, at least 50 bases, at least 100 bases, at least 1000 bases, or at least 10,000 bases. The sequence reads used in the methods described herein can be at most 10 bases, at most 30 bases, at most 50 bases, at most 100 bases, at most 1000 bases, or at most 10,000 bases.

The number or the average number of times that a particular nucleotide within the nucleic acid is read during the sequencing process (e.g., the sequencing depth) can be multiple times larger than the length of the nucleic acid being sequenced. In some instances, when the sequencing depth is sufficiently larger (e.g., by at least a factor of 5) than the length of the nucleic acid, the sequencing can be referred to as 'deep sequencing'. Sequencing the nucleic acid can comprise deep sequencing. For example, a nucleic acid can be sequenced such that the sequencing depth is about 20 times greater than the length of the nucleic acid. When the sequencing depth is at least about 100 times greater than the length of the nucleic acid, the sequencing can be referred to as 'ultra-deep sequencing'. Sequencing the nucleic acid can comprise ultra-deep sequencing. The sequencing depth can be one average at least about 5 times greater, at least about 10 times greater, at least about 20 times greater, at least about 30 times greater, at least about 40 times greater, at least about 50 times greater, at least about 60 times greater, at least about 70 times greater, at least about 80 times greater, at least about 90 times greater, at least about 100 times greater, or more than the length of the nucleic acid being sequenced.

Epigenetic Markers

Genomic sequence data can comprise epigenetic markers. Epigenetic markers can be any modification of a nucleic acid or an analyte associated with a nucleic acid that can affect gene transcription and/or affect protein expression. Epigenetic markers can be used to detect the presence and/or absence of chromosomal aberrations (e.g., copy number aberrations) in a subject. Non-limiting examples of epigenetic markers include nucleic acid methylation, nucleic acid hydroxymethylation, and histone modifications (e.g., acetylation and methylation of histone proteins). Changes in the pattern of methylation or hydroxymethylation can regulate nucleic acid-analyte binding, thereby effecting changes in gene expression and causing disease (e.g., cancer). These aberrant methylation patterns can be used to detect the presence of disease in a subject. Any of the diseases (e.g., cancer or tumor) disclosed herein can be detected. Any of the cancers disclosed herein can be acute or chronic. In some cases, the subject is not clinically diagnosed with cancer.

Epigenetic modifications, such as the chemical modification of nucleic acids (e.g., DNA methylation), the modification of an analyte associated with a nucleic acid (e.g., histones), or a change in the interaction between an analyte and a nucleic acid can affect the transcriptional efficiency of a given gene. Identification of correlations of either the presence or absence of one or more modification with a pathological state (e.g., a copy number aberration) can provide new methods for detecting, preventing, and/or prognosticating diseases in patients. The methods disclosed herein can comprise calculating a first value of at least one parameter. The at least one parameter can correspond to a transcriptional efficiency of at least a portion of the nucleic acid. Transcriptional efficiency can generally refer to the rate at which genomic material (e.g., DNA) is transcribed into protein-encoding RNA. Transcriptional efficiency can generally refer to an amount of protein-encoding RNA derived from genomic material. Translational efficiency can generally refer to the rate at which genomic material (e.g., DNA) is ultimately translated into proteins, or the rate at which any intermediate step in the process occurs. Translational efficiency can generally refer to an amount of protein derived from genomic material or RNA.

Mappability

Methods provided herein can comprise determining a "mappability" or "mappability score," which terms are used interchangeably herein for each of a plurality of genomic regions (e.g., genomic windows) of the reference genome. For each genomic region of the plurality of genomic regions, the methods can comprise using the mappability to determine a genomic region or subset of genomic regions of the plurality of genomic regions that does not meet a threshold value. The mappability of a genome can be determined by taking a genome, generating all possible reads of a given length, mapping those reads back to the genome, and identifying the percent of sequence reads that map uniquely to the genome at the expected location (e.g., the location where the sequence reads are generated from the genomic region). In some embodiments, the mappability of a genomic region can be determined as a percentage of the reads uniquely aligning within the genomic region. The mappability for a genome or genomic region can be 0%, about 10%, about 20%, about 30%, about 40%, about 50%, about 60%, about 70%, about 80%, about 90%, or 100%. The mappability for a genome or genomic region can be greater than 0%, greater than about 10%, greater than about 20%, greater than about 30%, greater than about 40%, greater than about 50%, greater than about 60%, greater than about 70%, greater than about 80%, greater than about 90%, or 100%. The mappability of a genome or genomic region can be 0% to about 10%, about 10% to about 20%, about 20% to about 30%, about 30% to about 40%, about 40% to about 50%, about 50% to about 60%, about 60% to about 70%, about 70% to about 80%, about 80% to about 90%, or about 90% to 100%.

Mappability analysis as described herein can be performed using existing tools/methods, such as those described on genome<dot>ucsc<dot>edu</>cgi-bin</>hgTrackUi?db=hg18&g=wgEncodeMapability. In some cases, the mappability score of a reference genome of a species can be determined once and available for different analyses on different biological samples of subjects of the same species. For instance, in some examples, the mappability score of a human reference genome can be available from existing databases, such as ENCODE at UCSC (genome<dot>ucsc<dot>edu</>ENCODE</>index<dot>html). The mappability score of a human reference genome can comprise a Broad alignability score, a Duke uniqueness score, CRG Alignability Configuration score, a Rosetta uniqueness score, or UMass uniqueness score. The Broad alignability score (e.g., Broad alignability track) can display whether a region is made up of mostly unique or mostly non-unique sequence. The Duke uniqueness score (e.g., Duke uniqueness track) can display how unique is each sequence on the positive strand starting at a particular base and of a particular length. The Duke excluded regions score (e.g., Duke excluded regions track) can display genomic regions for which mapped sequence tags are filtered out before signal generation and peak calling for Duke/UNC/UTA's Open Chromatin tracks. The Rosetta uniqueness score (e.g., Rosetta uniqueness track) can use sequence 'tiles' of 35 bp. The UMass uniqueness score (e.g., UMass uniqueness track) can display a uniqueness signal for each base which represents the sum of both plus and minus strand 15-mer occurrences of that particular 5'->3' (plus strand) sequence throughout the genome. The CRG Alignability score (e.g., CRG Alignability track) can display how uniquely k-mer sequences align to a region of the genome.

Sequence uniqueness within the genome can play a part when attempting to map next-generation short sequencing reads to a genome. Sequence uniqueness can be a factor that can introduce a bias in sequencing or its analysis—other factor can be GC content (GC-rich sequences, e.g., genic/exonic region, as well as very GC-poor regions can be under-represented, e.g., because of amplification steps in the protocol). Reads mapped to multiple regions can be discarded, genomic regions with high sequence degeneracy/low sequence complexity can therefore show lower mapped read coverage than unique regions, which can create a systematic bias.

Mappability can improve with increased read length and can generally show an inverse correlation with genomic repeats. One approach to increase coverage in regions of low mappability can be to use longer reads that improve the chance of a read encompassing a unique sequence that anchors all remaining sequences. A second approach can be to generate paired-end libraries with longer insert sizes, which can increase the chance of one read of the pair mapping to a unique region outside the repeat sequence. Mappability data can be used to normalize read depth, for example, when using depth of coverage to estimate DNA copy number.

Mappability can be determined by using a reference genome sequence, and generating all possible reads of a given length, and mapping those reads back to the reference genome to identify reads that map uniquely in the expected location.

Mappability Thresholds

The methods provided herein can comprise determining a mappability threshold for one or more genomic regions, e.g., genomic windows, e.g., of a reference genome. The mappability threshold can be 90% or less, 85% or less, 80% or less, 75% or less, 70% of less, 65% or less, 60% or less, 55% or less, 50% or less, 45% or less, 40% or less, 35% or less, 30% or less, 25% or less, 20% or less, 15% or less, 10% or less, 5% or less, or 0%. In some cases, the mappability threshold is about 85%. A genomic region (e.g., genomic window) that has a mappability below the mappability threshold can be a candidate for sequence assembly, e.g., local de novo assembly. (See e.g., FIG. 3A, 307). In some cases, mappability score of a reference genome can be determined "once for all," e.g., biological samples from the same species as the reference genome can be subject to the analysis using the same mappability score of the reference genome. In some cases, if the mappability threshold is determined, the genomic regions with mappability score below the threshold remain the same for each individual biological sample from subjects of the species. Local de novo assembly can then be performed on the same genomic regions with individualized sequence reads for each different pool of sequence reads obtained from individual biological sample.

Sequence Assembly

Methods provided herein can comprise performing de novo sequence assembly in one or more of the subsets of genomic regions. De novo sequence assembly can comprise assembling sequence reads, e.g., short sequence reads, to create full-length sequences without using a template. The methods provided herein can comprise performing a mapping sequence assembly in one or more of the subsets of genomic region. Local de-novo (LDN) sequence assembly can be performed in genomic regions having a mappability less than a given threshold. For example, de-novo sequencing can be performed in a genomic region having less than 90% mappability, less than 85% mappability, less than 80% mappability, less than 75% mappability, less than 70% mappability, less than 65% mappability, less than 60% mappability, less than 55% mappability, less than 50% mappability, less than 40% mappability, less than 30% mappability, or less than 20% mappability. LDN sequence assembly can be performed in genomic regions flanking (adjacent to) genomic regions having a mappability below the threshold. In some cases, the methods comprise LDN assembly of sequence reads aligning to genomic regions with mappability below the threshold and sequence reads aligning to genomic regions that have mappability above the threshold and are adjacent to the genomic regions with mappability below the threshold. The sequence reads used in the LDN assembly in a region can comprise sequence reads that uniquely map to the region of low mappability, or sequence reads that uniquely map to the region of low mappability and sequence reads that map to the region of low mappability but do not uniquely map to the region.

De-novo sequence assembly can be performed on a genomic region of any size. For example, LDN sequence assembly can be performed on a genomic region of about 500 kilobases (kb). LDN assembly can be performed in genomic regions of about 1 kb, about 5 kb, about 10 kb, about 20 kb, about 50 kb, about 100 kb, about 500 kb, about 1 megabase (Mb), about 5 Mb, about 10 Mb, about 50 Mb, about 100 Mb, about 500 Mb, or greater than about 5Mb. De-novo sequence assembly can be performed on a genomic region having a size within a range. For example, LDN sequence assembly can be performed on a genomic region having a size within a range of about 50 kb to about 150 kb. LDN assembly can be performed on genomic regions with a size range of about 90 kb to about 110 kb, about 80 kb to about 120 kb, about 70 kb to about 130 kb, about 60 kb to about 140 kb, about 50 kb to about 150 kb, about 40 kb to about 160 kb, about 30 kb to about 170 kb, about 20 kb to about 180 kb, about 10 kb to about 190 kb, about 10 kb to about 100 kb, about 50 kb to about 250 kb, about 100 kb to about 500 kb, about 250 kb to about 1 Mb, about 500 kb to about 2.5 Mb, about 1 Mb to about 10 Mb, about 5 Mb to about 25 Mb, about 10 Mb to about 50 Mb, about 0.5 kb to about 50Mb, about 10 kb to about 50 Mb, about 100 kb to about 50 Mb, about 0.5 kb to about 25 Mb, about 0.5 kb to about 10 Mb, or about 0.5 kb to about 1 Mb.

Performing LDN sequence assembly can improve genomic coverage of sequence reads that are subject for further analysis. In some cases, the genomic coverage in the genomic regions with a mappability below the threshold can be at least about 5%, at least about 10%, at least about 20%, at least about 30%, at least about 40%, at least about 50%, at least about 60%, at least about 70%, at least about 80%, at least about 90%, or at least about 100%. In some cases, the genomic coverage in the genomic regions with a mappability below the threshold can be about 10% to 30%, about 20% to about 50%, about 30% to about 60%, about 40% to about 50%, about 50% to about 80%, or about 60% to about 90%. In some cases, the genomic coverage in the genomic regions with a mappability below the threshold can be about 30% to about 50%. The methods can comprise generating genomic sequence data, e.g., combined sequence data, corresponding to the subject based at least in part on the aligned sequence reads and the de novo sequence assembly. The de novo sequence assembly can be performed in at least one genomic region adjacent to the one or more of the subsets of genomic regions. LDN assembly performed on these flanking regions can be used to assess the quality of the assembly performed within the region having a mappability below threshold.

The de novo sequence assembly can be performed using an algorithm, e.g., a greedy algorithm assembler or a graph method assembler. The greedy algorithm assembler can find local optima in alignments of smaller reads. The greedy algorithm assembler can include steps of pairwise distance calculation of reads; clustering of reads with greatest overlap; assembly of overlapping reads into larger contigs; and repeating these steps. The graph method assembler can be a string graph assembler or De Bruijn graph assembler. The De Bruijn graph method assembler can be Spades, which can be a single-cell genome assembler. The de novo sequence assembly can be performed using Ray. Ray can include Ray, RayMeta, RayCommunities, Ray Ontologies, and Ray Surveyor. Ray can be a distributed scalable assembler. The de novo assembly can be performed usingABySS. AByss can be a de novo, parallel, paired-end sequence assembler that can be used for the assembly of short sequence reads. ABySS can be ABySS for genomic assembly or Trans-ABySS, for transcriptomic assembly. The de novo sequence assembly can be performed using ALL-PATHS-LG. ALLPATHS-LG can handle large sequence repeats, correct errors, use data from jumping libraries, and assemble low coverage regions. The de novo sequence assembly can be performed using Trinity. The de novo sequence assembly can be performed using HGAP, which can be a long read assembler that can make use of sequencing data from technologies from PACBIO; see e.g., Chin et al. Nonhybrid, finished microbial genome assemblies from long-read SMRT sequencing data. *Nature Methods* 10, no. 6 (2013): 563-569. The de novo sequence assembly can be performed using Falcon, which can be a long read assembler that e.g., makes use of sequencing data from technologies from PACBIO (see e.g., Chin et al. Phased diploid genome assembly with single-molecule real-time sequencing. *Nature Methods* 13, no. 12 (2016): 1050-1054). The de novo sequence assembly can be performed using Canu, which can be a long read assembler that can, e.g., make use of sequencing data from technologies from PACBIO or OXFORD NANOPORE; see e.g., Koren et al. Canu: scalable and accurate long-read assembly via adaptive k-mer weighting and repeat separation. *Genome research* 27, no. 5 (2017): 722-736. The de novo sequence assembly can be performed using Hinge, which can be a long read assembler that can make use of sequencing data from technologies from PACBIO or OXFORD NANOPORE; see e.g., Kamath et al. HINGE: long-read assembly achieves optimal repeat resolution. *Genome research* 27, no. 5 (2017): 747-756. The de novo sequence assembly can be performed using Euler SR USR, which can include an error correction mode. The de novo sequence assembly can be performed using MIRA, which can be a general purpose assembler that can integrate various platform data and perform true hybrid assemblies. The de novo sequence assembly can be performed using SOAP de novo, which can be an all purpose genome assembler. The de novo sequence assembly can be performed using Velvet. The de novo sequence assembly can be performed using Minia, which can be a de Bruijn graph assembler that can be optimized for very low memory usage. The de novo sequence assembly can be performed using CLC Cell, which can be based on a de Bruijn graph approach. The de novo sequence assembly can be performed using Newbler.

The algorithm can comprise an overlap graph. An overlap graph can represent the sequence reads and their overlaps. The algorithm can comprise a K-mer graph. The K-mer graph can comprise nodes, representing fixed-length sequences and can comprise edges, representing fixed-length overlaps between subsequences. In some cases, the K-mer graph does not require all-against-all overlap discovery and it does not store individual reads or their overlaps. The K-mer graph can compress redundant sequences. The algorithm can comprise a de Bruijn graph approach or an Eulerian approach. The K-mer graph can be a de Bruijn graph, and it can contain an Eulerian path, that is, a path that traverses each edge exactly once. The algorithm can comprise an all-against-all, pair-wise read comparison. The algorithm can comprise an approximate read layout generated by construction and manipulation of an overlap graph. The algorithm can apply a filter to the reads before it builds a graph. The algorithm can comprise multiple sequence alignment (MSA) that can determine the precise layout and the consensus sequence.

The algorithm can, given any read or contig, add one more read or contig, and can repeat this operation until no more operations are possible. In other words, the algorithm can, in a first operation, calculate pairwise alignments of all fragments; in a second operation, choose two fragments with the largest overlap; and in a third operation, merge the chosen fragments. The algorithm can then repeat the second and third operation until only one fragment is left. The algorithm can use a read-correcting pre-processor. The algorithm can distribute a K-mer graph, and graph computations, across a compute grid, whose combined memory can be large, in order to address memory limitation capabilities.

The algorithm can comprise at least one or more of the following features: modeled features of reads, base substitutions, homopolymer miscount, concentrated error in 3' end, flow space, color space, removal of erroneous reads, correction of erroneous base calls, filter overlaps, greedy contig extension, collapse simple paths, erosion of spurs, transitive overlap reduction, bubble smoothing, simple paths as graph nodes, reads as graph nodes, K-mers as graph nodes, multiple values of K, multiple overlap stringencies, approaches to graph reductions, approaches to graph construction, or any combination thereof. The algorithm can be based on K-mer frequencies, K-mer frequencies and a numeric quality value (QV), and/or alignments.

Sequence reads can be assembled into contigs by various methods, such as use of algorithms for the de novo assembly of a plurality of sequence reads. The algorithm for assembling sequence reads can be Overlap-Consensus Assembly. Overlap-Consensus Assembly can use the overlap between sequence reads to create a link between them. The sequence reads can be generally linked by regions that overlap enough that non-random overlap can be assumed. Linking together sequence reads in this way can produce a contig or an overlap graph in which each node corresponds to a read and an edge represents an overlap between two sequence reads. Assembly with overlap graphs is described, for example, in U.S. Pat. No. 6,714,874, which is hereby incorporated herein by reference in its entirety.

De novo assembly can proceed according to so-called greedy algorithms. For assembly according to greedy algorithms, one of the sequence reads of a group of sequence reads can be selected, and it can be paired with another read with which it exhibits a substantial amount of overlap—it can be paired with the read with which it exhibits the most overlap of all of the other sequence reads. Those two sequence reads can be merged to form a new read sequence, which can then be put back in the group of sequence reads and the process can be repeated. Assembly according to a greedy algorithm is described, for example, in Schatz, et al., Genome Res., 20:1165-1173 (2010) and U.S. Pub. 2011/0257889, each of which is hereby incorporated herein by reference in its entirety.

In some embodiments, assembly proceeds by pairwise alignment, for example, exhaustive or heuristic (e.g., not exhaustive) pairwise alignment. Exhaustive pairwise alignment, sometimes called a "brute force" approach, can calculate an alignment score for every possible alignment between every possible pair of sequences among a set. Assembly by heuristic multiple sequence alignment can ignore certain mathematically unlikely combinations and can be computationally faster. One heuristic method of assembly by multiple sequence alignment is the so-called "divide-and-conquer" heuristic, which is described, for example, in U.S. Pub. 2003/0224384, which is hereby incorporated herein by reference in its entirety. Another heuristic method of assembly by multiple sequence alignment is progressive alignment, as implemented by the program ClustalW (see, e.g., Thompson, et al., Nucl. Acids. Res., 22:4673-80 (1994)). Assembly by multiple sequence alignment in general is discussed in Lecompte, 0., et al., Gene 270:17-30 (2001); Mullan, L. J., Brief Bioinform., 3:303-5 (2002); Nicholas, H. B. Jr., et al., Biotechniques 32:572-91(2002); and Xiong, G., Essential Bioinformatics, 2006, Cambridge University Press, New York, N.Y., each of which is hereby incorporated herein by reference in its entirety.

Assembly by alignment can proceed by aligning sequence reads to each other or by aligning sequence reads to a reference. For example, by aligning each read, in turn, to a reference genome, all of the sequence reads can be positioned in relationship to each other to create the assembly.

One method of assembling reads into contigs that can be used in the methods provided herein involves making a de Bruijn graph. De Bruijn graphs can reduce the computation effort by breaking reads into smaller sequences of DNA, called k-mers, where the parameter k denotes the length in bases of these sequences. In a de Bruijn graph, all reads can be broken into k-mers (all subsequences of length k within the reads) and a path between the k-mers can be calculated. In assembly according to this method, the reads can be represented as a path through the k-mers. The de Bruijn graph can capture overlaps of length k−1 between these k-mers and not between the actual reads. Thus, for example, the sequencing CATGGA can be represented as a path through the following 2-mers: CA, AT, TG, GG, and GA. The de Bruijn graph approach can handle redundancy well and can make the computation of complex paths tractable. By reducing the entire data set down to k-mer overlaps, the de Bruijn graph can reduce the high redundancy in short-read data sets. The maximum efficient k-mer size for a particular assembly can be determined by the read length as well as the error rate. The value of the parameter k can have significant influence on the quality of the assembly. Estimates of good values can be made before the assembly, or the optimal value can be found by testing a small range of values. Assembly of reads using a de Bruijn graph is described, e.g., in U.S. Patent App. Pub. No. 2011/0004413, U.S. Patent App. Pub. No. 2011/0015863, and U.S. Patent App. Pub. No. 2010/0063742, each of which is incorporated herein by reference in their entirety.

Other methods of assembling sequence reads into contigs according to the methods provided herein are possible. For example, the sequence reads can contain barcode information inserted into template nucleic acid during sequencing. Sequence reads can be assembled into contigs by reference to the barcode information. For example, the barcodes can be identified and the sequence reads can be assembled by positioning the barcodes together.

Assembly can proceed by making reference to supplied information about the expected position of the various reads relative to each other. This information can be obtained, for example, if the subject nucleic acid being sequenced has been captured by molecular inversion probes, because the start of each sequence read can derive from a genomic position that is known and specified by the probe set design. Each sequence read can be collected according to the probe from which it was designed and positioned according to its known relative offset. Information about the expected position of sequence reads relative to each other can be supplied by knowledge of the positions (e.g., within a gene) of an area of nucleic acid amplified by primers. For example, sequencing can be done on amplification product after a number of regions of the target nucleic acid are amplified using primer pairs designed or known to cover those regions. Sequence reads can then be positioned during assembly at least based on which primer pair was used in an amplification that lead to those reads. Assembly of reads into contigs can proceed by any combination or hybrid of methods including the above-referenced methods.

One or more computer programs can be used for assembling reads. The one or more computer assembly programs can run on a single general-purpose computer, on a cluster or network or system of computers, or on one or more specialized computing devices dedicated to sequence analysis.

Assembly can be implemented, for example, by the program 'The Short Sequence Assembly by k-mer search and 3' read Extension' (SSAKE), which can be from Canada's Michael Smith Genome Sciences Centre (see e.g., Vancouver, B.C., Calif.) (see, e.g., Warren, R., et al., Bioinformatics, 23:500-501 (2007)). SSAKE can cycle through a table of sequence reads and search a prefix tree for the longest possible overlap between any two sequences. SSAKE can cluster reads into contigs. Another read assembly program is Forge Genome Assembler, which can be from Darren Platt and Dirk Evers and available, e.g., through the SourceForge web site maintained by Geeknet (Fairfax, Va.) (see, e.g., DiGuistini, S., et al., Genome Biology, 10:R94 (2009)). Forge can distribute its computational and memory consumption to multiple nodes, if available, and can assemble large sets of reads. Forge can be written in C++ using the parallel MPI library. Forge can handle mixtures of reads, e.g., Sanger, 454 sequence (Roche), and Illumina reads. Assembly through multiple sequence alignment can be performed, for example, by the program Clustal Omega, (see e.g., Sievers F., et al., Mol Syst Biol 7 (2011)), ClustalW, or ClustalX (see e.g., Larkin M. A., et al., Bioinformatics, 23, 2947-2948 (2007)) available from University College Dublin (Dublin, Ireland). Sequence read assembly can also be performed with the programs from the package SOAP, available, e.g., through the website of Beijing Genomics Institute (Beijing, CN) or BGI Americas Corporation (Cambridge, Mass.). For example, the SOAP denovo program can implement a de Bruijn graph approach. SOAP3/GPU can align short reads to a reference sequence.

Another read assembly program that can be used in the methods provided herein is ABySS, which can be from Canada's Michael Smith Genome Sciences Centre (Vancouver, B.C., Calif.) (see e.g., Simpson, J. T., et al., Genome Res., 19(6):1117-23 (2009)). ABySS can use the de Bruijn graph approach and can run in a parallel environment. Read assembly can also be done by Roche's GS De Novo Assembler, known as gsAssembler or Newbler (NEW assemBLER), which can be designed to assemble sequence reads from the Roche 454 sequencer (described, e.g., in Kumar, S. et al., Genomics 11:571(2010) and Margulies, et al., Nature 437:376-380 (2005)) or from Sanger sequencing. Newbler can accept 454 Flx Standard sequence reads and 454 Titanium sequence reads as well as single and paired-end sequence reads and optionally Sanger sequence reads. Newbler can be run on Linux, in either 32 bit or 64 bit versions. Newbler can be accessed via a command-line or a Java-based GUI interface.

Other read assembly programs that can be used in the methods provided herein include RTG Investigator from Real Time Genomics, Inc. (San Francisco, Calif); iAssembler (see e.g., Zheng, et al., BMC Bioinformatics 12:453 (2011)); TgiCL Assembler (see e.g., Pertea, et al., Bioinformatics 19(5):651-52 (2003)); Maq (Mapping and Assembly with Qualities), which can be by Heng Li, available for download, e.g., through the SourceForge website maintained, e.g., by Geeknet (Fairfax, Va.); MIRA3 (Mimicking Intelligent Read Assembly), described e.g., in Chevreux, B., et al., Genome Sequence Assembly Using Trace Signals and Additional Sequence Information, 1999, Computer Science and Biology: Proceedings of the German Conference on Bioinformatics (GCB) 99:45-56; PGA4genomics (described e.g., in Zhao F., et al., Genomics. 94(4):284-6 (2009)); and Phrap (described, e.g., in de la Bastide, M. and McCombie, W. R., Current Protocols in Bioinformatics, 17:11.4.1-11.4.15 (2007)). CLC cell can be a de Bruijn graph-based computer program for sequence read mapping and de novo assembly of NGS reads, which can be available from CLC bio Germany (Muehltal, Germany). The assembly program MaSuRCA can be used in the methods provided herein. MaSuRCA can make use of sequence information from sequence technologies from ILLUMINA, PACBIO, OXFORD NANOPORE, 454 sequencing, and Sanger data and is described, e.g., at Zimin et al, The MaSuRCA genome Assembler. *Bioinformatics* 2013 or Zimin et al. Hybrid assembly of the large and highly repetitive genome of *Aegilops tauschii,* a progenitor of bread wheat, with the mega-reads algorithm. *Genome Research* (2017) doi: 10.1101/gr.213405.116.

Assembly of sequence reads can produce one or more contigs. In the case of homozygous or single target sequencing, a single contig can be produced. In the case of a heterozygous diploid target, a rare somatic mutation, or a mixed sample, for example, two or more contigs can be produced. Each contig can include information from the reads that make up that contig. Assembling the reads into contigs can be conducive to producing a consensus sequence corresponding to each contig. In certain embodiments, a consensus sequence can refer to the most common, or predominant, nucleotide at each position from among the assembled reads. A consensus sequence can represent an interpretation of the sequence of the nucleic acid represented by that contig.

PCR Normalization

In some cases, methods provided herein comprise using a probe-based detection assay, e.g., a microarray, and can comprise normalizing the one or more intensity measurements, obtained by the hybridization of the labeled cell-free nucleic acid molecules, using a covariate of GC content. The method can comprise performing statistical smoothing on the one or more intensity measurements. The method can comprise identifying a chromosomal aberration in the absence of identification of one or more single nucleotide polymorphisms (SNPs) in the plurality of cell-free nucleic acid molecules.

A PCR normalization method can be used as a step in methods provided herein. See, e.g., Freeman et al., Genome Res. 16:949-61 (2006), and Nannya et al., Cancer Res. 65:6071-9 (2005)). PCR normalization can employ quadratic correction using the covariates of GC content of PCR fragments and length of PCR fragments. For instance, implementation of this approach in the software Chromosome Copy Number Analysis Tool (CNAT) Version 4.0, which is a software that can help visualize the identification of amplifications, deletions, and loss of heterozygosity (LOH), can use the singular value decomposition method. The normalization can be performed via a linear model fit and can also combine the two different covariates or predictors in a single equation, as shown below via q(x,y). The correction can be implemented in two steps as shown via equation p(x). In one example, the equations are as follows:

$$\Lambda_i^{1,2} = \log_2\left(\frac{S_i^1}{S_i^2}\right) \text{ for } ith \text{ fragment}$$

$$\Lambda_i^{1,2} = {}^c\Lambda_i^{1,2} + p(x)$$

$$p(x) = \sum_{j=1}^{2}(a_j + b_j x_j + c_j x_j^2) \text{ where}$$

$$j = GC, \text{ fragment length}$$

$$q(x, y)) = (A + bx + b'y + cx^2 + c'y^2) \text{ where}$$

$$x = GC/y = \text{fragment length}$$

Where $A_i^{1,2}$ represents the corrected copy number, p(x) represents PCR amplification kinetics and x1 and x2 represent the length and GC content of the fragment of interest and coefficients a1, a2, b1, b2, c1 and c2 can be determined by a series of linear regressions from the observed $\log_2$ ratios. A more robust, non-linear regression can be performed. This can make a significant difference to fitting the tails of the distribution.

Noise Reduction (By, e.g., Gaussian Smoothing)

Methods provided herein can comprise a step of reducing noise in, e.g., copy number estimates, e.g., across a genome. Gaussian smoothing can be performed prior to performing a Markov model (e.g., Hidden Markov Model (HMM)) based segmentation and/or prior to identifying a chromosomal aberration, e.g., copy number variation, in the subject. Smoothing can increase the signal to noise ratio in the data (e.g., the estimate of copy number across the genome) and can enhance the demarcation between regions of copy number change. The degree of smoothing can be governed by the experimental question being addressed, e.g., the genomic footprint of the aberrations being detected. Filters that can be used include Gaussian, Spline, and Lowess. Gaussian smoothing can be referred to as an explicit filter since the HMM can inherently perform a smoothing operation.

If Gaussian smoothing is performed, the user can set a smoothing bandwidth, also known as a smoothing parameter, or the algorithm to dynamically determine a smoothing bandwidth based on the underlying genomic data (e.g., the distribution of genomic modifications such as epigenetic modifications). Smoothing can be performed on the PCR normalized (and inter-array normalized when virtual arrays are being used) copy number data. Smoothing can be performed for every index modification by considering the copy number contributions from all flanking genomic modifications encompassed in a window (W), as defined by:

$$W \approx 2 * \sigma_{mult} * \sigma$$

Here, G corresponds to the Gaussian bandwidth and $\sigma_{mult}$ is the sigma-multiplier. Specifically, all flanking genomic modifications within the bounds defined by $\sigma_{mult} * \sigma$ to the left and right of the genomic modification can be considered. Note that $\sigma_{mult}$ is a user defined number but can be set to a fixed default value of, for example, 2. The default of 2 can be comparable to the full-width-at half-maximum of the filter.

The choice of smoothing bandwidth can affect the level of variance (noise) reduction obtained in the data (e.g., the estimate of copy number across the genome). The smoothing operation can preserve the overall trend in the data, but the level of smoothing can mask micro-aberrations and a smaller sigma (less than 100 KB) can be used in some cases. When the sumLog option, which can be optimized for bias, is used, Gaussian smoothing can facilitate variance reduction. If sumLog is the operational mode, minimal smoothing of the order of 15 kB can contribute significantly to improvement in signal to noise reduction. The modulation of sigma can be interconnected with the modulation of the HMM parameters, e.g., the standard deviation discussed below.

The methods described herein can make use of one or more different types of kernels for smoothing. The kernel can be parabolic (Epanechinikov), Tricube, or Gaussian. In some cases, a nearest neighbor smoother or kernel average smoother is used.

GC Normalization

GC normalization can be performed in the methods provided herein, e.g., after reducing noise using Gaussian kernel smoothing. The GC normalization can be global or local; local GC normalization can be defined by some boundary criteria. Sequence read or fragment counts and GC counts can be binned, e.g., to a selected bin-size. A curve describing the conditional mean fragment count per GC value can be estimated by, e.g., binning or assuming smoothness. The resulting GC curve can determine a predicted count for each bin based on the bin's GC. The predictions can be used directly to normalize the original signal or as the rates for a heterogeneous Poisson model.

Markov Models

Methods provided herein can comprise segmenting the genomic sequence data, e.g., the combined sequence data, using a Markov model statistical analysis to identify the chromosomal aberration in the subject. The Markov model statistical analysis can be a Hidden Markov model statistical analysis. The Hidden Markov model can comprise an ergodic model. The ergodic model can comprise a plurality of states.

The genomic sequence data, e.g., the combined sequence data, can be segmented into at least one copy number state. The copy number state can be selected from a copy number loss state, a copy number gain state, and/or a copy number normal state. The copy number state can comprise the copy number normal state. A variability of the copy number normal state can be determined using at least one of a healthy reference sample and a disease reference sample. The disease reference sample can be a tumor reference sample. The disease reference sample can be a reference sample of any of the diseases disclosed herein.

Figure 2:
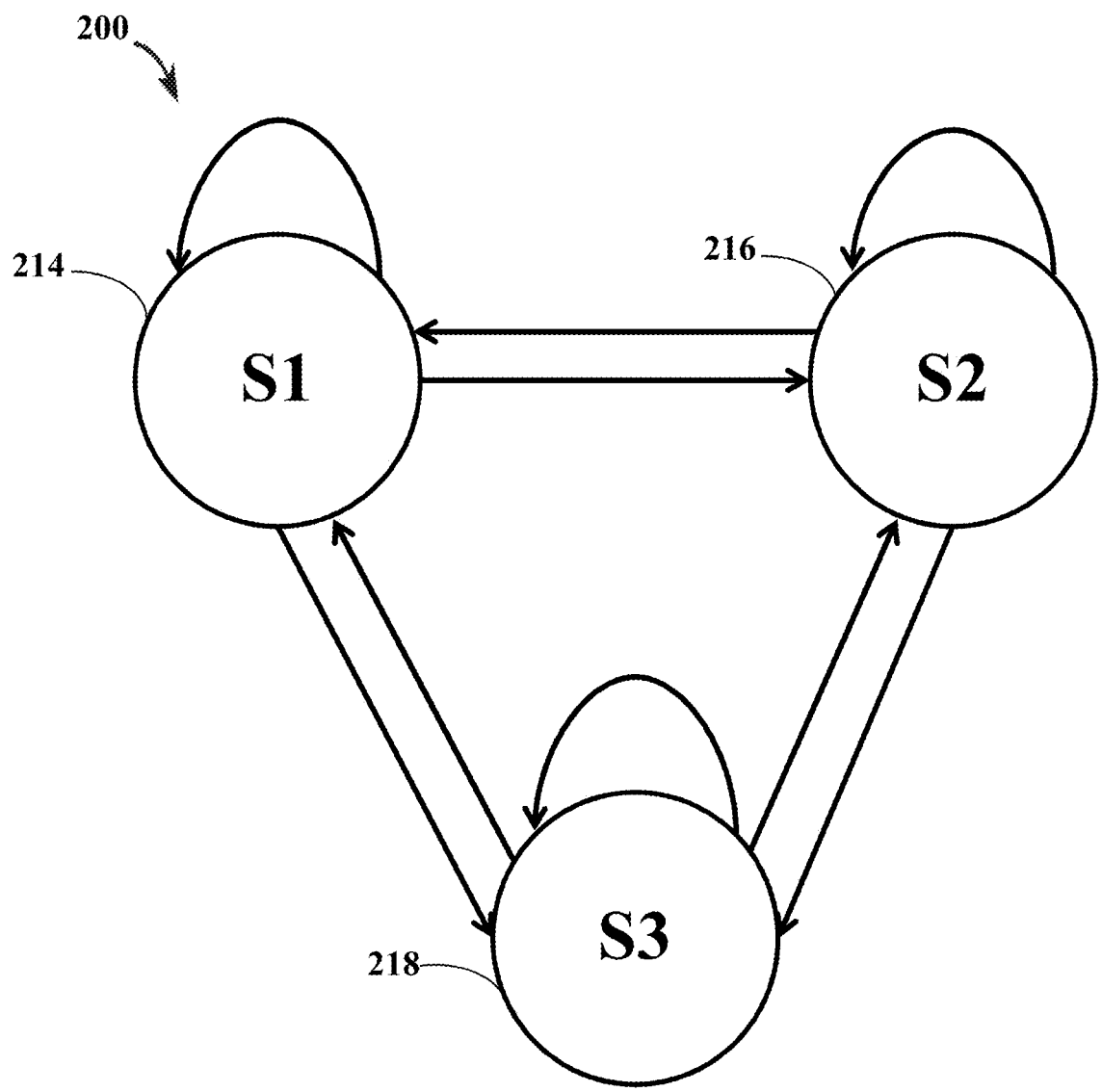
FIG. 2 illustrates an ergodic Hidden Markov model comprising 3 states and the state transition probabilities, represented by arrows.

The hidden Markov model (HMM) can be a statistical model where the system being modeled is assumed to be a Markov process with unknown parameters, and the challenge can be to determine the hidden parameters from the observable parameters. The extracted model parameters can then be used to perform further analysis, for example, for pattern recognition applications. The MINI can be considered as the simplest dynamic Bayesian network. In a regular Markov model, the state can be directly visible to the observer, and the state transition probabilities can be the only parameters. In some cases, in the hidden Markov model (HMM), the state is not directly visible, but variables influenced by the state can be visible. Each state can have a probability distribution over the possible output values. Therefore the sequence of values generated by the MINI can provide some information about the sequence of states. The HMM can be applied in temporal pattern recognition, such as speech, handwriting, gesture recognition and bioinformatics. See e.g., Lior Pachter and Bernd Sturmfels, Algebraic Statistics for Computational Biology, Cambridge University Press, 2005, ISBN 0-521-85700-7, Eddy, Nature Biotechnology 22:1315-1316 (2005) and Pavel Pevzner, Computational Molecular Biology: An Algorithmic Approach, MIT Press, 2000, especially pp. 145-149. See also, Rabiner, L, A Tutorial on Hidden Markov Models and Selected Applications in Speech Recognition, Proceedings of the IEEE, Vol 77, pp 257-86. (1989), each of which are incorporated herein by reference in their entireties. The HMM can be defined by a set of hidden states, a matrix of state transition probabilities and a matrix of emission probabilities. Each hidden state can have different statistical properties. Transitions from one state to any other state can be possible. An exemplary ergodic 3-state model 200 is shown in FIG. 2, wherein each arrow represents the probabilities of transitions between a first state (S1) 214, a second state (S2) 216, and a third state (S3) 218.

Ergodic theory can be a mathematical concept wherein a measure-preserving transformation T on a probability space is said to be ergodic if the only measurable sets invariant under T have measure 0 or 1. Another term for this property is metrically transitive. Ergodic theory can be the study of ergodic transformations. Ergodic theory can form the basis for the work now referred to as chaos theory.

Applications of Methods Provided Herein

The methods provided herein can be used to determine a presence or absence of a condition in a subject. The condition can be associated with one or more copy number aberrations identified using a method described herein. The condition can be a cancer described herein.

The methods provided herein can be used to determine the tissue of origin of cell-free nucleic acid molecules from a biological sample, e.g., cell-free nucleic acid molecules from a plasma or serum sample from the subject. The tissue of origin can be a healthy tissue or a diseased tissue, e.g., a cancer (see e.g., Qui et al. (2017) Genome-wide copy number variation pattern analysis and a signature for non-small cell lung cancer *Genes Chromosomes Cancer* 56: 559-569). The tissue of origin of the cell-free nucleic acid molecules can be determined based on one or more copy number aberrations identified using a method described herein.

The methods provided herein can be used to monitor a condition, e.g., cancer, or monitor a therapy, e.g., a therapy for treating a cancer. The methods provided herein can be used to determine a treatment option for a subject, e.g., determining one or more drugs that can be administered to a subject with a condition, e.g., cancer. For example, the methods provided herein can be used to analyze copy number aberrations over time for a subject.

Exemplary Workflow

The present disclosure provides a framework, e.g., a Markov model based framework, that can be used to quantify chromosomal aberrations (e.g., copy number aberrations and loss of heterozygosity). The Markov model based framework can be a Hidden Markov Model (HMM) based framework. An exemplary 3-step method for identifying copy number aberrations using a framework, e.g., a Hidden Markov Model (HMM) based framework, is shown in FIGS. 3A-C.

Figure 3A:
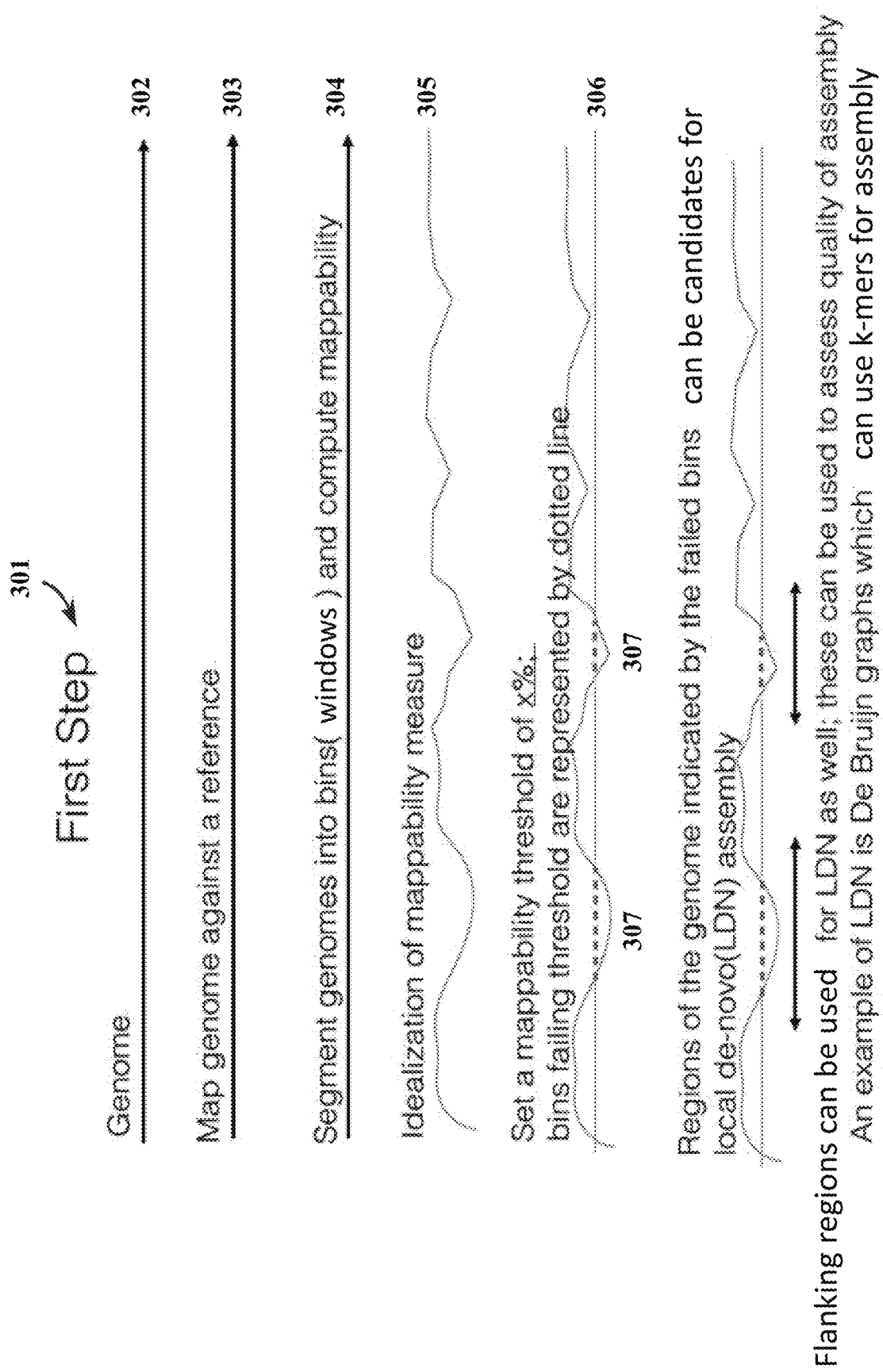

In a first step (301), as shown in FIG. 3A, regions of the genome (302) with less than desired levels of mappability are identified. To determine mappability across the genome, reads are generated by breaking down a reference genome. After determining a location of the reads in a reference genome, e.g., by aligning (303) the reads to a reference genome and determining a location of the reads in the reference genome, mappability can be determined (304) for given locations or genomic regions (e.g., defined by windows or bins) across the genome. The mappability (305) can then be compared against a threshold (306) to determine if the mappability corresponding to a given genomic location or region is sufficient (e.g., above threshold). For regions of the genome having a mappability below threshold (307), local de novo (LDN) assembly of sequence reads of nucleic acid molecules from a biological sample can be performed.

Figure 3B:
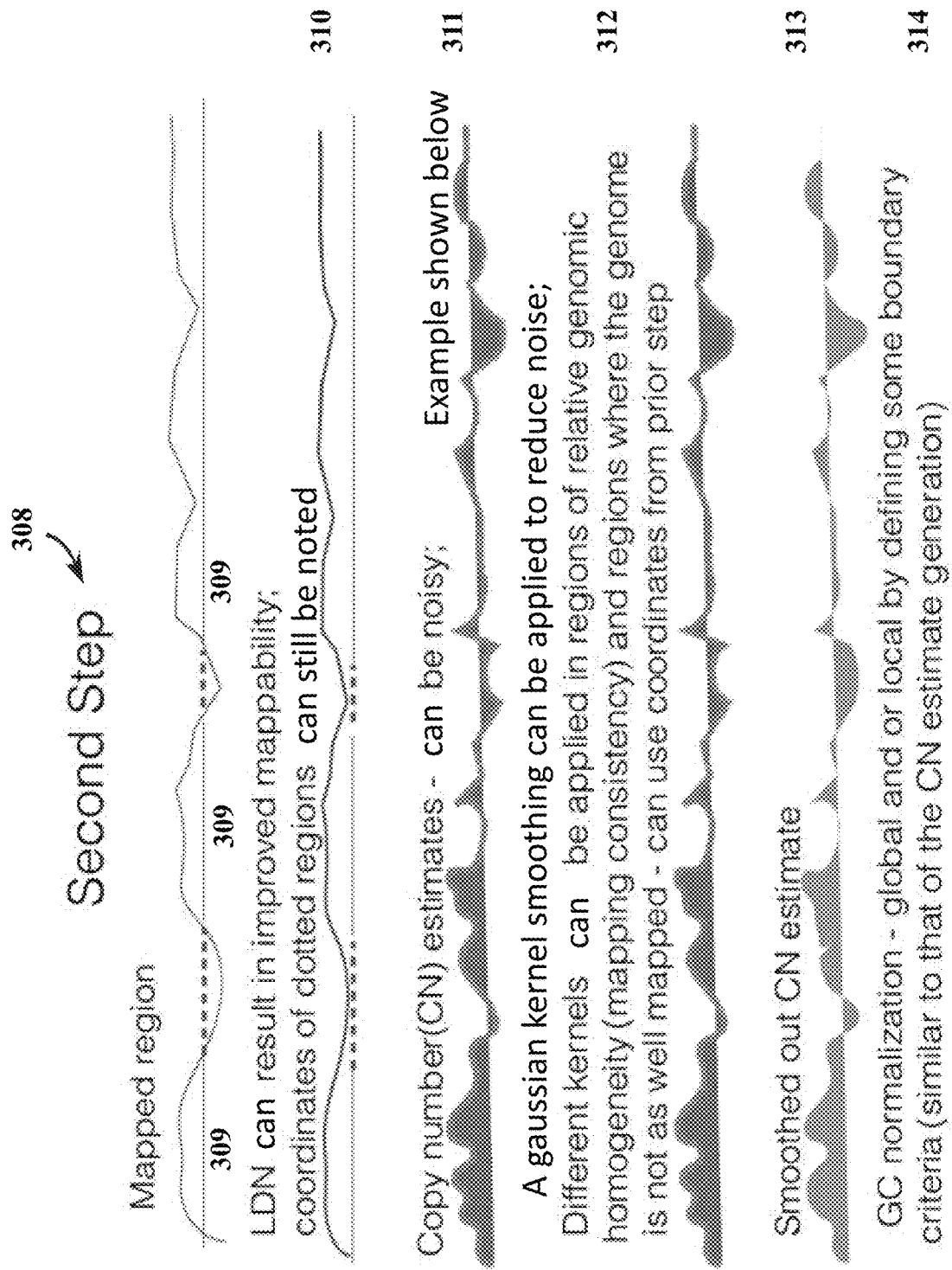

In a second step (308), as shown in FIG. 3B, local de novo assembly, Gaussian kernel smoothing and/or GC content normalization can be used to estimate a copy number at given genomic location across the genome. LDN assembly can be performed not only on the genomic region having a mappability below threshold, but also the genomic regions flanking (309) (e.g., on either side) of the genomic region having a mappability below threshold. LDN assembly performed on these flanking regions can be used to assess the quality of the assembly performed within the region having a mappability below threshold. After performing LDN assembly to increase the mappability (310) within regions previously having below-threshold mappability, noise reduction by, e.g., Gaussian smoothing (312) and (313), can be performed to reduce the noise in the copy number estimates. The copy number can be estimated by counting the number of sequence reads aligning to a particular region of the genome. In some cases, the copy number can be determined relative to a different region of the genome (e.g., a number of sequence reads aligning to a first genomic region normalized to a number of sequence reads aligning to a second genomic region). When applying Gaussian smoothing to the initial copy number estimates across the genome, different kernels or the same kernels can be used in regions of having similar genomic homogeneity. When applying Gaussian smoothing to the initial copy number estimates across the genome, different kernels or the same kernels can be used in regions having varying genomic homogeneity. The copy number estimate for a given region can be further refined by normalizing (314) the copy number to the GC content of the given genomic region.

In a third step (315), as shown in FIG. 3C, an ergodic model can be used to estimate the likelihood that a given genomic region contains a copy number gain (e.g., amplification) or copy number loss (e.g., deletion). The ergodic model can be used to estimate the likelihood that a given genomic region does not contain a copy number gain or copy number loss. In a 3 state model (e.g., copy number amplification, copy number deletion, diploid), the probability that a given genomic region will transition to a different state can depend on a variety of factors. Different factors (e.g., if there is a family history of cancer, or if the subject has been exposed to a particular carcinogen) can be used to adjust the probability of a given genomic region transiting from a first state to a second state. An expectation maximization algorithm (e.g., a Viterbi algorithm) can be used to determine the maximum likelihood that a given genomic region belongs to a given state of the model (e.g., exhibits a copy number amplification, copy number deletion, or is diploid), or to identify hidden states (e.g., the Viterbi path) based on the observed state.

Use of the methods disclosed herein can significantly improve the copy-number estimation. The accuracy of delineating change-points, where change points correspond to switching in copy number states, can be enhanced by adopting a Hidden Semi-Markov framework where the duration density for the genomic modifications in each of the states can be explicitly modeled. Loss of heterozygosity (LOH) and aberrant copy number regions can be derived from both paired (tumor-normal) and unpaired samples. The analysis can correlate the association and the extent of localization of the copy number and LOH changes. Estimation of LOH changes can be possible via an ethnicity matched or unmatched and family matched or unmatched manner. For copy number analysis, such methods can provide a genome-wide estimation of the copy-number status in normal, paired tumor-normal and tumor versus pooled normal samples.

Apart from HMM, methods and systems of the present disclosure can be used with other statistical approaches, such as, for example, other stochastic models. For example, a statistical model can be used which models randomly changing systems where it is assumed that future states depend only on the current state and not on the events that occurred before it.

Computer Systems

Figure 4:
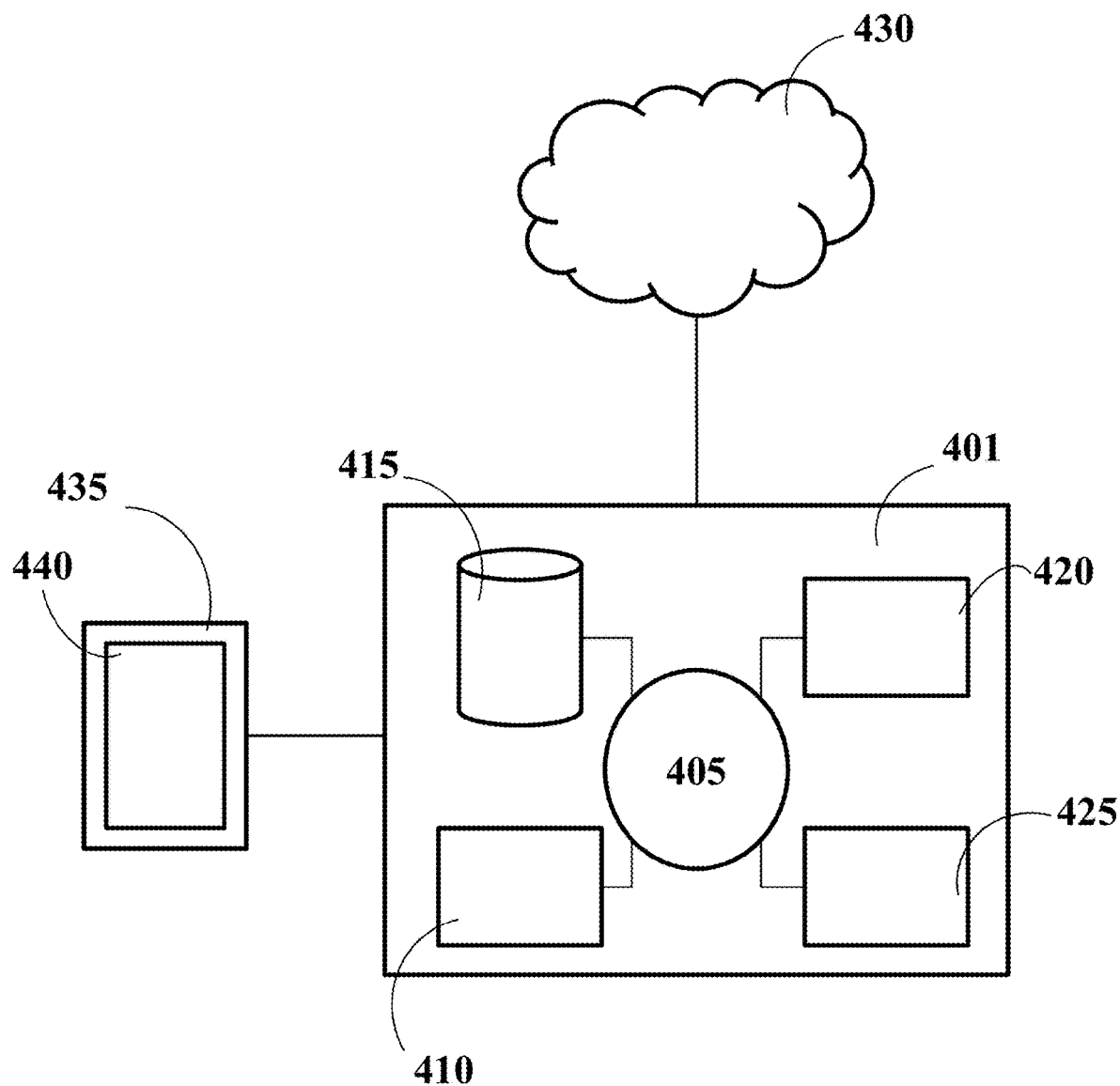
FIG. 4 shows a computer system that is programmed or otherwise configured to implement methods provided herein.

The present disclosure provides computer systems that are programmed to implement methods of the disclosure. FIG. 4 shows a computer system 401 that is programmed or otherwise configured to detect chromosomal aberrations in a subject, e.g., using a Hidden Markov model. The computer system 401 can regulate various aspects of methods for detecting chromosomal aberrations of the present disclosure, such as, for example, parameters for the Hidden Markov model and/or the detection of genomic regions having a mappability below a threshold. The computer system 401 can be an electronic device of a user or a computer system that is remotely located with respect to the electronic device. The electronic device can be a mobile electronic device.

The computer system 401 can include a central processing unit (CPU, also "processor" and "computer processor" herein) 405, which can be a single core or multi core processor, or a plurality of processors for parallel processing. The computer system 401 can also include memory or memory location 410 (e.g., random-access memory, read-only memory, flash memory), electronic storage unit 415 (e.g., hard disk), communication interface 420 (e.g., network adapter) for communicating with one or more other systems, and peripheral devices 425, such as cache, other memory, data storage and/or electronic display adapters. The memory 410, storage unit 415, interface 420 and peripheral devices 425 can be in communication with the CPU 405 through a communication bus (solid lines), such as a motherboard. The storage unit 415 can be a data storage unit (or data repository) for storing data. The computer system 401 can be operatively coupled to a computer network ("network") 430 with the aid of the communication interface 420. The network 430 can be the Internet, an internet and/or extranet, or an intranet and/or extranet that is in communication with the Internet. The network 430 in some cases is a telecommunication and/or data network. The network 430 can include one or more computer servers, which can enable distributed computing, such as cloud computing. The network 430, in some cases with the aid of the computer system 401, can implement a peer-to-peer network, which can enable devices coupled to the computer system 401 to behave as a client or a server.

The CPU 405 can execute a sequence of machine-readable instructions, which can be embodied in a program or software. The instructions can be stored in a memory location, such as the memory 410. The instructions can be directed to the CPU 405, which can subsequently program or otherwise configure the CPU 405 to implement methods of the present disclosure. Examples of operations performed by the CPU 405 can include fetch, decode, execute, and writeback.

The CPU 405 can be part of a circuit, such as an integrated circuit. One or more other components of the system 401 can be included in the circuit. In some cases, the circuit is an application specific integrated circuit (ASIC).

The storage unit 415 can store files, such as drivers, libraries and saved programs. The storage unit 415 can store user data, e.g., user preferences and user programs. The computer system 401 in some cases can include one or more additional data storage units that are external to the computer system 401, such as located on a remote server that is in communication with the computer system 401 through an intranet or the Internet.

The computer system 401 can communicate with one or more remote computer systems through the network 430. For instance, the computer system 401 can communicate with a remote computer system of a user. Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 401 via the network 430.

Methods as described herein can be implemented by way of machine (e.g., computer processor) executable code stored on an electronic storage location of the computer system 401, such as, for example, on the memory 410 or electronic storage unit 415. The machine executable or machine readable code can be provided in the form of software. During use, the code can be executed by the processor 405. In some cases, the code can be retrieved from the storage unit 415 and stored on the memory 410 for ready access by the processor 405. In some situations, the electronic storage unit 415 can be precluded, and machine-executable instructions are stored on memory 410.

The code can be pre-compiled and configured for use with a machine having a processor adapted to execute the code, or can be compiled during runtime. The code can be supplied in a programming language that can be selected to enable the code to execute in a pre-compiled or as-compiled fashion.

Aspects of the systems and methods provided herein, such as the computer system 401, can be embodied in programming. Various aspects of the technology can be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which can provide non-transitory storage at any time for the software programming. All or portions of the software can at times be communicated through the Internet or various other telecommunication networks. Such communications, for example, can enable loading of the software from one computer or processor into another, for example, from a management server or host computer into the computer platform of an application server. Thus, another type of media that can bear the software elements includes optical, electrical and electromagnetic waves, such as used across physical interfaces between local devices, through wired and optical landline networks and over various air-links. The physical elements that carry such waves, such as wired or wireless links, optical links or the like, also can be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, can take many forms, including but not limited to, a tangible storage medium, a carrier wave medium or physical transmission medium. Non-volatile storage media include, for example, optical or magnetic disks, such as any of the storage devices in any computer(s) or the like, such as can be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media can take the form of electric or electro-magnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer can read programming code and/or data. Many of these forms of computer readable media can be involved in carrying one or more sequences of one or more instructions to a processor for execution.

The computer system 401 can include or be in communication with an electronic display 435 that comprises a user interface (UI) 440. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 405. The algorithm can, for example, perform de novo sequence assembly and/or identify genomic regions of low mappability.

EXAMPLES

Example 1

Detection of a Copy Number Aberration in a Blood Sample

A plurality of nucleic acid molecules is isolated from a blood sample of a patient. The nucleic acid molecules are cell-free, that is, they do not comprise any cellular material and/or cells. The plurality of nucleic acid molecules is amplified and sequenced. The mappability of a plurality of genomic regions of the sequenced nucleic acid molecule sample is determined. A de novo sequence assembly in the genomic regions is performed. The combined sequence data is segmented using a Hidden Markov model and a copy number aberration is detected.

Example 2

Detection of a Copy Number Aberration Using a 3-State Ergodic Model

A blood sample is obtained from a human patient and is centrifuged to separate plasma from remaining blood components (e.g., red blood cells, white blood cells and platelets). Cells are removed from plasma by centrifugation for 5 minutes at 1,000-2,000×g using a refrigerated centrifuge. Centrifugation for 15 minutes at 2,000×g depletes platelets in the plasma sample. Following centrifugation, the plasma sample is immediately transferred into a clean polypropylene tube using a Pasteur pipette. The sample is maintained at 2-8° C. while handling. Cell-free DNA fragments in the plasma sample are amplified using polymerase chain reaction (PCR), and subsequently sequenced to obtain sequence reads corresponding to the cell-free nucleic acid fragments in the plasma sample. The sequence reads are aligned to a reference genome, and the number of sequence reads aligning to each genomic location is counted to determine a mappability of various genomic regions across the genome. The mappability is compared against a reference value to identify genomic regions having a mappability below threshold. De-novo sequence assembly is performed using a de Bruijn graph based k-mer based assembler within the genomic regions identified as having a mappability below threshold, in addition to genomic regions on either side (e.g., flanking regions) of the genomic region having a mappability below threshold. De novo sequence assembly results in an improved genomic coverage of the sequence reads that are used for copy number analysis. A first copy number estimate is determined based on the alignment of the sequence reads to the de-novo assembled reference genome. Assuming a Gaussian distribution of read coverage, a Gaussian smoothing operation is performed to reduce noise (e.g., from sequencing errors, structural rearrangements or insertions or deletions in the reference) in the first copy number estimate. Genomic regions which have an AT/GC imbalance (e.g., a high/low AT content, or a high/low GC content) can have spurious sequence similarities resulting in low mappability. Accordingly, a GC content normalization is performed to reduce noise in the copy number variation estimate from misalignment of sequence reads to the reference genome due to AT/GC imbalance. The Gaussian smoothed, GC-content normalized copy number estimate data is entered into a 3-state HMM-based ergodic model to determine if a chromosomal aberration exits at given regions in the genome. The 3 states include amplification, deletion and diploid, and the probability of a given region transitioning from a first state to a second state is adjusted based on a family history of cancer. An expectation maximization algorithm such as the Viterbi algorithm is used to determine the most likely path of hidden states that results in the observed state, corresponding to the Gaussian smoothed, GC-content normalized copy number estimate data.

Example 3

Mappability Analysis of Reference Genome hg19

Figure 5:
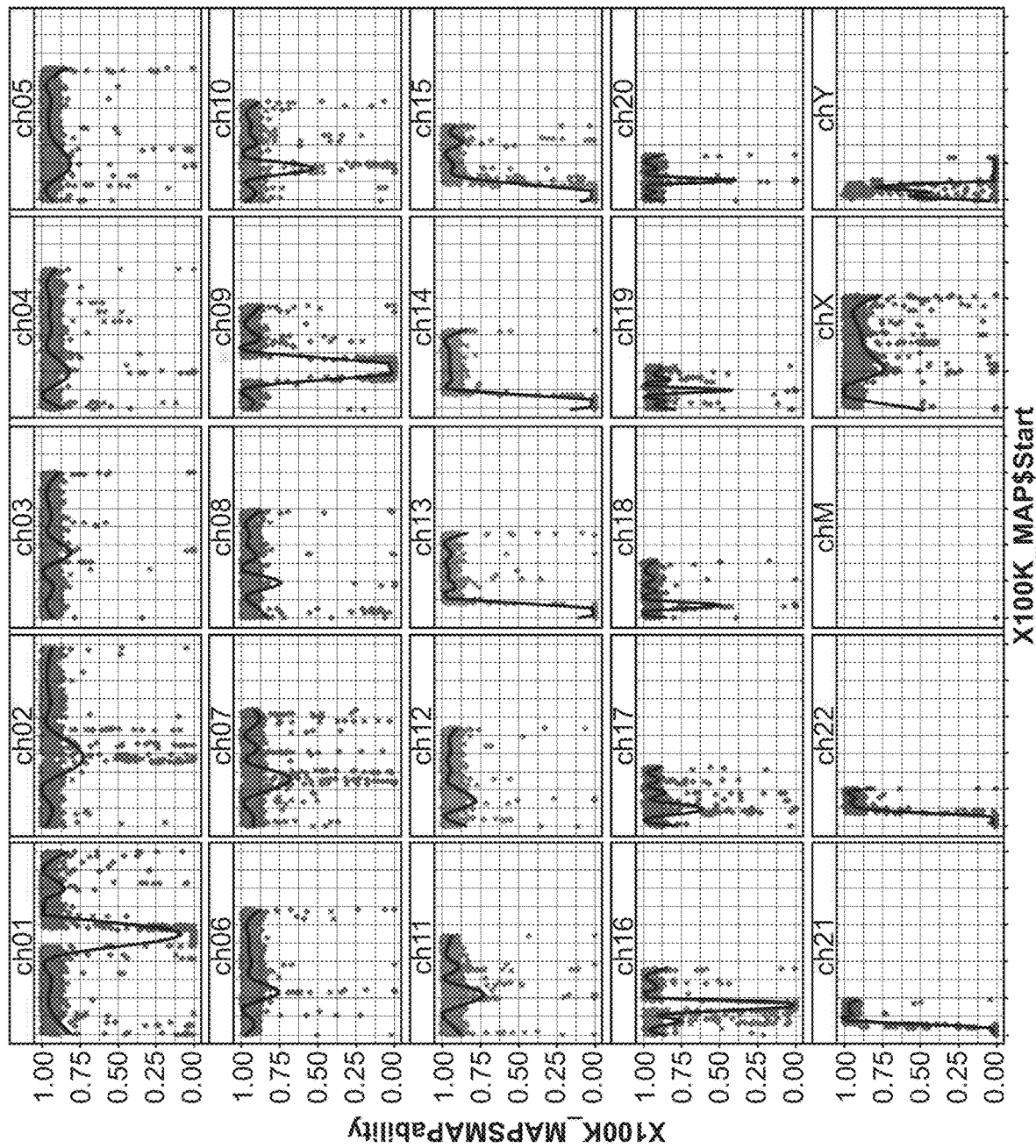
FIG. 5 illustrates results of an exemplary mappability analysis on a human reference genome.

In this example, mappability analysis was performed on an exemplary human reference genome, Homo sapiens genome assembly GRCh37 (hg19). The reference genome hg19 was binned in 100kB, and mappability was assessed in each bin. FIG. 5 shows plots of the mappability of all the bins on different chromosomes, which are represented by individual dots. As shown in the figure, majority of the bins have high mappability values, like above 75% (0.75), while there are also a number of bins having low mappability values. When a mappability threshold was taken as 85% (0.85), then about 5.5% of the genome was below the threshold and would be removed from follow-on sequencing analysis, and incremental loss of the genomic coverage was about 1% if the threshold was adjusted from 0.5 to 0.85. When the mappability threshold was set as 0.85, about 6.5% (150/2277 100kB bins) of chromosome 1 (Chr1) was below the threshold, and about 2.8% (40/1400 100 kB bins) of Chr8 was below the threshold. Based on the analysis, lower mappability bins were generally at telomeres or centromeres. Other than the telomeres and centromeres, other low mappability bins were mostly non-contiguous, ranging from a contiguity of 300 kB -1000 kB.

Example 4

Improvement of Genomic Coverage

In this example, paired-end sequence reads from test biological samples from human subjects were subject to copy number analysis according to an exemplary method provided herein. With the mappability analysis performed as described in Example 1, anchor points genomic bins with mappability below the threshold of 0.85 as well as their flanking bins which passed the threshold were identified and taken as candidates of local de novo assembly. Raw sequence reads that overlap with and are contained within the anchors from test samples were grouped for local assembly (using De Bruijn graph algorithm), after which contigs were formed. Scaffolds were created by appropriate ordering of contigs based on the paired-end information of the reads and filling the gaps between the contigs. The scaffolds and the bins passing the thresholds were then subsumed into copy number analysis. In this example, about 30 to about 50% of the genomic region covered by the bins that failed the threshold was "restored," i.e. sequence reads that map to about 30 to about 50% of the genomic region covered by the bins that failed the threshold were picked up and subject to the copy number analysis.

An alternative approach to improve genomic coverage is to lowering the mappability thresholds. In this example, noise level was compared when mappability threshold and read depth were adjusted. Sequence reads from 40 normal biological samples of healthy human subjects were subject to copy number estimation without LDN sequence assembly. Noise level, % CV (coefficient of variation) of copy number estimates, was calculated across 40 normal samples for each 1 MB genomic bin. FIG. 7 shows distribution graphs of the genomic bins over different %CV value. Labeled at the top of the figure is the read depth (1×, 1.5×, 2×, 3×, 4×, or 5×) for each graph, and at the right of the figure is the mappability threshold (0.5, 0.65, 0.7, 0.8, or 0.85) applied for each graph (each individual analysis). FIG. 6 is a plot showing the mean %CV value versus mappability threshold that was applied for the analysis (map_thresh). Each line demonstrates a different analysis done with a different read depth. As a general trend, the higher read depth generated the lower CV value.

Other Embodiments

The methods provided herein can be generalizable to a multi-state model, for example, beyond the 3 states described herein. One example of the multi-state embodiment can be a 5 state model. For example, 2 states can be used for deletions (e.g., homozygous or deletion of 2 copies, and heterozygous or deletion of 1 copy). The copy neutral state can constitute a 3rd state. The 4th and 5th states can be assigned to amplifications of 1 or 2 copies.

It is to be understood that the methods, devices, or systems described herein can vary. It is also to be understood that the terminology used herein is for the purpose of describing particular embodiments only, and is not intended to limit the scope of the methods and compositions described herein, which will be limited only by the appended claims. While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein can be employed in practicing the disclosure. It is intended that the following claims define the scope of the disclosure and that methods and structures within the scope of these claims and their equivalents be covered thereby.

Several aspects are described with reference to example applications for illustration. Unless otherwise indicated, any embodiment can be combined with any other embodiment. It should be understood that numerous specific details, relationships, and methods are set forth to provide a full understanding of the features described herein. A skilled artisan, however, will readily recognize that the features described herein can be practiced without one or more of the specific details or with other methods. The features described herein are not limited by the illustrated ordering of acts or events, as some acts can occur in different orders and/or concurrently with other acts or events. Furthermore, not all illustrated acts or events are required to implement a methodology in accordance with the features described herein.

Some inventive embodiments herein contemplate numerical ranges. When ranges are present, the ranges include the range endpoints. Additionally, every sub range and value within the rage is present as if explicitly written out. The term "about" or "approximately" can mean within an acceptable error range for the particular value as determined by one of ordinary skill in the art, which will depend in part on how the value is measured or determined, e.g., the limitations of the measurement system. For example, "about" can mean within 1 or more than 1 standard deviation, per the practice in the art. Alternatively, "about" can mean a range of up to 20%, up to 10%, up to 5%, or up to 1% of a given value. Alternatively, particularly with respect to biological systems or processes, the term can mean within an order of magnitude, within 5-fold, or within 2-fold, of a value. Where particular values are described in the application and claims, unless otherwise stated the term "about" meaning within an acceptable error range for the particular value can be assumed.

The section headings used herein are for organizational purposes only and are not to be construed as limiting the subject matter described.

What is claimed is:

1. A method of analyzing nucleic acid molecules from a biological sample of a subject of an organism, the method comprising:
  (a) obtaining, in a computer system, sequence reads of the nucleic acid molecules from the biological sample of the subject, wherein the nucleic acid molecules comprise cell-free nucleic acid molecules;
  (b) identifying, in the computer system, a first genomic region in a reference genome of the organism with a mappability score below a threshold and a second genomic region in the reference genome of the subject with a mappability score above the threshold, wherein (i) the second genomic region is adjacent to one end of the first genomic region, (ii) the mappability score of a genomic region is expressed as the fraction of all possible reads of a specified length that map to the genomic region, and (iii) the specified length is a length of at least 10 nucleotides;
  (c) performing, in the computer system, local de novo assembly of a first subset of the sequence reads that align to the first genomic region and a second subset of the sequence reads that align to the second genomic region, thereby generating contigs, wherein at least one of the contigs extends over a portion of the first genomic region and a portion of the second genomic region; and
  (d) recovering, in the computer system, sequence data corresponding to the contigs within the first genomic region, wherein the recovered genomic sequence data comprise at least a portion of the first subset of sequence read.

2. The method of claim 1, further comprising identifying a third genomic region in the reference genome having a mappability score above the threshold, wherein the third genomic region is located on the other end of the first genomic region, wherein the contigs are generated by local de novo assembly of the first subset, the second subset, and the third subset of the sequence reads, and wherein at least one of the contigs extends over a portion of the first genomic region and a portion of the third genomic region.

3. The method of claim 1, wherein the reference genome comprises a plurality of genomic regions, and the method further comprises:
  (e) repeating steps (b)-(d) for each of the genomic regions having a mappability score below the threshold, thereby recovering portions of the sequence data from all of the genomic regions having mappability scores below the threshold.

4. The method of claim 3, further comprising:
  combining the recovered sequence data from (e) with sequence data from genomic regions that have mappability scores above the threshold.

5. The method of claim 4, further comprising:
  normalizing the combined sequence data using a covariate of GC content.

6. The method of claim 4, further comprising:
  segmenting the combined sequence data to identify a chromosomal aberration.

7. The method of claim 6, wherein the combined sequence data is segmented into a copy number state, the copy number state selected from the group consisting of a copy number loss state, a copy number gain state, and a copy number normal state.

8. The method of claim 7, wherein the copy number state comprises the copy number normal state, and wherein a variability of the copy number normal state is determined using at least one of a healthy reference sample and a tumor reference sample.

9. The method of claim 6, wherein the segmenting comprises using hidden Markov model statistical analysis.

10. The method of claim 6, wherein said chromosomal aberration comprises a copy number aberration.

11. The method of claim 10, wherein the copy number aberration is from a tumor.

12. The method of claim 6, wherein said chromosomal aberration is identified in the absence of identifying one or more single nucleotide polymorphisms in said nucleic acid molecules.

13. The method of claim 1, wherein the local de novo assembly is performed using an algorithm selected from the group consisting of a greedy algorithm assembler, graph method assembler, string graph assembler, De Bruijn graph assembler, Spades, Ray, ABySS, ALLPATHS-LG, and Trinity.

14. The method of claim 1, wherein the local de novo assembly comprises creation of a scaffold comprising the contigs, and wherein the recovered sequence data align to the scaffold.

15. The method of claim 14, wherein the sequence reads comprise paired-end sequence reads, and the scaffold is created by ordering the contigs based on paired-end information of the paired-end sequence reads.

16. The method of claim 1, wherein the recovered sequence data comprise sequence reads that align uniquely to the contigs within the first genomic region.

17. The method of claim 1, wherein the mappability score of the first genomic region and the second genomic region is determined according to the following:
  partitioning the first genomic region into a first plurality of partitioned sequences and the second genomic region into a second plurality of partitioned sequences, and determining the mappability score of the first genomic region based, at least in part, on a first percentage of the first plurality of partitioned sequences that uniquely align to the first genomic region, and the mappability score of the second genomic region based, at least in part, on a second percentage of the second plurality of partitioned sequences that uniquely align to the second genomic region.

* * * * *